(12) United States Patent
Saffell et al.

(10) Patent No.: US 10,775,338 B2
(45) Date of Patent: Sep. 15, 2020

(54) ELECTROCHEMICAL GAS SENSOR, FILTER AND METHODS

(71) Applicant: ALPHASENSE LIMITED, Braintree, Essex (GB)

(72) Inventors: John Saffell, Cambridge (GB); Ronan Baron, Cambridgeshire (GB); Marlene Hossain, Essex (GB)

(73) Assignee: ALPHASENSE LIMITED, Braintree (GB)

( * ) Notice: Subject to any disclaimer, the term of this patent is extended or adjusted under 35 U.S.C. 154(b) by 0 days.

(21) Appl. No.: 15/401,704

(22) Filed: Jan. 9, 2017

(65) Prior Publication Data

US 2017/0276634 A1 Sep. 28, 2017

(30) Foreign Application Priority Data

Mar. 22, 2016 (EP) .................................... 16161782

(51) Int. Cl.
*G01N 27/40* (2006.01)
*G01N 33/00* (2006.01)
(Continued)

(52) U.S. Cl.
CPC ......... *G01N 27/40* (2013.01); *G01N 27/4045* (2013.01); *G01N 27/413* (2013.01);
(Continued)

(58) Field of Classification Search
CPC ........ G01N 27/406–41; G01N 33/0004–0075; G01N 27/40; G01N 33/0014;
(Continued)

(56) References Cited

U.S. PATENT DOCUMENTS 4,221,761 A * 9/1980 Bullens .................. B01D 53/56
422/54
5,187,137 A * 2/1993 Terui .................. B01D 53/8675
502/241
(Continued)

FOREIGN PATENT DOCUMENTS

CN 101571506 11/2009
DE 196 22 931 12/1997
(Continued)

OTHER PUBLICATIONS

Yoshio et al. (JP 2005/046701 A, machine translation) (Year: 2005).*
(Continued)

*Primary Examiner* — Maris R Kessel
*Assistant Examiner* — Joshua L Allen
(74) *Attorney, Agent, or Firm* — Nixon & Vanderhye P.C.

(57) ABSTRACT

The invention relates to an electrochemical gas sensing apparatus for sensing one or more analytes, such as $NO_2$ and/or $O_3$, in a sample gas and a method of using same. The apparatus uses $Mn_2O_3$ as a filter for ozone. The $Mn_2O_3$ may take the form of a powder which may be unmixed, mixed with various PTFE particles sizes, formed into a solid layer deposited onto a membrane and/or pretreated with $NO_2$.

20 Claims, 17 Drawing Sheets

(51) Int. Cl.
*G01N 27/404* (2006.01)
*G01N 27/413* (2006.01)

(52) U.S. Cl.
CPC ..... *G01N 33/0014* (2013.01); *G01N 33/0024* (2013.01); *G01N 33/0037* (2013.01); *G01N 33/0039* (2013.01); *G01N 33/0059* (2013.01); *Y02A 50/245* (2018.01); *Y02A 50/247* (2018.01)

(58) Field of Classification Search
CPC ........... G01N 27/4045; G01N 33/0024; G01N 27/413; G01N 33/0037; G01N 33/0039; G01N 33/0059; Y02A 50/245; Y02A 50/247
See application file for complete search history.

(56) References Cited

U.S. PATENT DOCUMENTS

| | | | |
|---|---|---|---|
| 5,262,129 A | 11/1993 | Terada | |
| 5,342,786 A * | 8/1994 | Capuano | G01N 30/06 422/78 |
| 6,051,436 A * | 4/2000 | Reagen | G01N 21/631 436/106 |
| 2005/0145493 A1* | 7/2005 | Saffell | G01N 27/4045 204/431 |
| 2007/0269346 A1* | 11/2007 | Wohltjen | G01N 33/0014 422/83 |
| 2011/0048108 A1* | 3/2011 | Yamagishi | G01N 33/0037 73/31.06 |
| 2011/0201123 A1* | 8/2011 | Watson | G01N 33/0039 436/135 |
| 2011/0290672 A1* | 12/2011 | Mett | B82Y 15/00 205/781 |
| 2012/0164035 A1* | 6/2012 | Yoshida | B01D 53/8675 422/211 |
| 2014/0311905 A1 | 10/2014 | Stetter | |

FOREIGN PATENT DOCUMENTS

| | | |
|---|---|---|
| DE | 103 30 704 | 12/2004 |
| EP | 1 544 614 | 6/2005 |
| EP | 2 975 390 A1 | 1/2016 |
| GB | 2 436 144 | 9/2007 |
| JP | 57-56748 | 4/1982 |
| JP | 2005-46701 | 2/2005 |
| JP | 2005046701 A * | 2/2005 |

OTHER PUBLICATIONS

Penrose et al. (WR Penrose, L Pan, JR Stetter, WM Ollison, Sensitive measurement of ozone using amperometric gas sensors, Analytica Chimica Acta 313 (1995) 209-219). (Year: 1995).*

Knake et al. (R Knake, PC Hauser, Sensitive electrochemical detection of ozone, Analytica Chimica Acta 459 (2002) 199-207) (Year: 2002).*

Search Report dated Oct. 30, 2015 issued in corresponding European Application No. 15176730.8 (18 pgs.).

Viricelle J. P. et al. *Selectivity improvement of semi-conducting gas sensors by selective filter for atmospheric pollutants detection*. Materials Science and Engineering C, Elsevier Science S.A. CH, vol. 26, No. 2-3, Dec. 1, 2005, pp. 186-195 (10 pgs.).

*Potentiostat circuit for D2 combined CO and H2S sensor*, Alphasense, Internet citation: www.alphasense.com, Mar. 1, 2007, pp. 1-3 (3 pgs.).

Wako NPL (MnO2 purity, http://www.e-reagent.com/uh/Sks.do?pcode=13-0968&now=1511148422479&JE=E&pop_zenkai_gst=1, revised Nov. 3, 2006) (1 pg.).

Hossain, Marlene et al., "Differentiating $NO_2$ and $O_3$ at Low Cost Air Quality Amperometric Gas Sensors", Alphasense Ltd., Great Notley, Essex, UK, 2016 American Chemical Society, Oct. 28, 2016 (4 pgs.).

* cited by examiner (A)

(B)

(A)

(B)

(A)

(B)

(A)

(B)

ELECTROCHEMICAL GAS SENSOR, FILTER AND METHODS

This application claims priority to EP Patent Application No. 16161782.4 filed Mar. 22, 2016, the entire content of which is hereby incorporated by reference.

FIELD OF THE INVENTION

The invention relates to an electrochemical gas sensing apparatus for sensing a gaseous analyte, characterised by a filter for ozone and methods for making and using such apparatus.

BACKGROUND TO THE INVENTION

In order to measure atmospheric pollutants which may be present in air at low concentrations e.g. less than 5 or 10 ppb, it is necessary to provide air monitoring instruments which are sensitive, specific and which perform reliably for a long period of time.

One way to provide specificity is to provide a filter between an inlet into electrochemical gas sensing apparatus and the sensing electrode, where the filter is selected to remove one or more gas species which may otherwise interfere with measurements of the target analyte gas.

It has been proposed to use $MnO_2$ as a filter material in a conductometric sensor to filter $O_3$ out of ambient air (Viricelle J P et al., Materials Science and Engineering C, Elsevier Science S. A., CH, vol. 26, no. 2-3, pages 186-195). EP 2975390 (Alphasense Limited) proposed the use of an $MnO_2$ filter adjacent one of two carbon sensing electrodes which receive gas in parallel, in a sensor for the detection of $NO_2$ and/or $O_3$, without interference from $SO_2$, CO, NO, $NH_3$ and $H_2$.

Although $MnO_2$ is useful as a filter material to filter $O_3$ out of ambient air, for example in a sensor for the detection of $NO_2$ and/or $O_3$, it can create a problem with cross-sensitivity to NO. Without wanting to be bound by theory, we hypothesize that NO reacts with $MnO_2$ to form $NO_2$ which then reacts at the sensing electrode.

Accordingly, the invention seeks to provide an improved sensor for the detection of at least one gaseous analyte. Some embodiments relate to the detection of $NO_2$ and/or $O_3$.

SUMMARY OF THE INVENTION

According to a first aspect of the invention there is provided electrochemical gas sensing apparatus for sensing at least one gaseous analyte and comprising a housing having an inlet, a sensing electrode and an ozone filter interposed between the sensing electrode and the inlet, wherein the ozone filter comprises $Mn_2O_3$.

The at least one gaseous analyte is sensed (where present) in a gas sample, which may be air (typically adjacent the sensing apparatus). The ozone filter is interposed between the sensing electrode and the inlet such that the ozone filter filters gas (from a gas sample) received through the inlet before it reaches the sensing electrode. Typically, there is a gas path (along which gas flows and/or diffuses in use) extending between the inlet and the sensing electrode, and the ozone filter is located in the gas path. It may be that all gas received through the inlet passes through the ozone filter before it reaches the sensing electrode.

The at least one gaseous analyte may be $NO_2$ and/or $O_3$. The electrochemical gas sensing apparatus may be electrochemical gas sensing apparatus for sensing $NO_2$ and/or $O_3$.

The electrochemical gas sensing apparatus may have one or more outputs which output an electrical signal (e.g. current, or potential or a digital value) related to the concentration of the one or more analytes. The sensing electrode (and the second sensing electrode where present) is therefore typically an electrode at which $NO_2$ is reducible. Our further discussion will focus on the detection of $NO_2$ and/or ozone. However, the at least one analyte may comprise another gas, for example the least one analyte may be or comprise $SO_2$.

Mn has a degree of oxidation of IV in $MnO_2$ and III in $Mn_2O_3$. $Mn_2O_3$ is therefore a less strong oxidising agent and has distinct chemistry to $MnO_2$. Despite this we have surprisingly found that it is useful as an ozone filter in a practical sensor for detecting $NO_2$ and/or $O_3$ because of the possibility of forming a sensor with a low cross-sensitivity to NO. It may be that the gas sample comprises NO. It may be that the gas sample comprises a higher concentration of NO than $NO_2$. This commonly occurs in atmospheric gas monitoring and means that NO cross-sensitivity is particularly important.

It may be that the ozone filter comprises (or consists of) $Mn_2O_3$ powder.

It may be that the $Mn_2O_3$ (e.g. $Mn_2O_3$ powder) is $NO_2$ treated. Thus, the $Mn_2O_3$ (e.g. $Mn_2O_3$ powder) may have been treated with $NO_2$. The $Mn_2O_3$ (e.g. $Mn_2O_3$ powder) may as a result have $NO_2$ adsorbed to the surface thereof. The $Mn_2O_3$ (e.g. $Mn_2O_3$ powder) may be substantially $NO_2$ saturated. We have found that this improves the reliability of readings of measurements of the concentration of $NO_2$ in sensing apparatus for detecting $NO_2$ and/or $O_3$. It may be that the (treated) $Mn_2O_3$ (e.g. $Mn_2O_3$ powder) has at least $10^{12}$ molecules of $NO_2$ adsorbed thereto per $cm^2$ of surface.

It may be that at least $2 \times 10^{12}$ molecules of $NO_2$ are adsorbed per $cm^2$ of surface. The surface area is typically as determined by BET (Brunauer-Emmett-Teller (BET) theory).

It may be that at least 2, or at least 3, or at least 4 moles of $NO_2$ are adsorbed per gram of $Mn_2O_3$.

The ozone filter may comprise $Mn_2O_3$ powder mixed with binder.

Surprisingly, we have found that the decrease in sensitivity at low temperature is reduced where the $Mn_2O_3$ (e.g. $Mn_2O_3$ powder) is mixed with binder than if the filter comprises only $Mn_2O_3$ (e.g. $Mn_2O_3$ powder). Furthermore, NO cross sensitivity may be reduced when $Mn_2O_3$ (e.g. $Mn_2O_3$ powder) is mixed with binder rather than unmixed. Without wanting to be bound by theory, we hypothesize this can reduce the rate at which NO may be converted to $NO_2$ by the $Mn_2O_3$ (e.g. $Mn_2O_3$ powder) within the filter while still providing sufficient ozone filtering capacity.

Typically, the $Mn_2O_3$ powder makes up less than 50%, less than 25%, less than 20% or less than 15% by mass of the combined mass of the $Mn_2O_3$ and the binder (in the mixture of $Mn_2O_3$ and binder).

Typically, the $Mn_2O_3$ powder makes up greater than 5% or greater than 8% of the combined mass of the $Mn_2O_3$ and the binder (in the mixture of $Mn_2O_3$ and binder).

For example, the $Mn_2O_3$ powder may make up 8% to 20%, 8-17% or 8-15% of the combined mass of the $Mn_2O_3$ and the binder (in the mixture of $Mn_2O_3$ and binder).

It may be that the $Mn_2O_3$ powder is mixed with binder such as to reduce the available $Mn_2O_3$ surface area per unit of surface area of the inlet at least 4-fold or at least 10-fold.

It may be that the $Mn_2O_3$ powder is mixed with binder such that the available $Mn_2O_3$ surface area, as measured by BET analysis, per unit of cross-sectional area of the filter (perpendicular to the gas path through the filter) is less than 0.8 m² per cm², or less than 0.5 m² per cm², or less than 0.3 m² per cm². It may be that the $Mn_2O_3$ powder is mixed with binder such that the available $Mn_2O_3$ surface area, as measured by BET analysis, per unit of cross-sectional area of the filter is at least 0.015 m² per cm² at least 0.02 m² per cm², at least 0.025 m² per cm², at least 0.05 m² per cm², or at least 0.1 m² per cm².

The binder may comprise particles. The particles may be polytetrafluoroethylene (PTFE) particles. The binder may for example, be alumina or a silicate. The binder may assist by occupying volume so that the active surface area of the $Mn_2O_3$ powder per volume of gas space in the filter is reduced.

The $Mn_2O_3$ powder may be in the form of particles with a mean diameter of 5 to 100 microns. The $Mn_2O_3$ powder may be in the form of particles with a mean diameter of 25 to 75 microns.

The binder particles may have a mean diameter of 25 to 1500 microns. The binder particles may comprise PTFE particles having a mean diameter of greater than 100 but less than 1500 microns, or greater than 500 but less than 1500 microns, for example.

The $Mn_2O_3$ powder may coat the binder particles. The binder particles may be coated with $Mn_2O_3$ powder.

Where the ozone filter comprises a mixture $Mn_2O_3$ powder and a particulate binder, the mixture of particles is preferably provided in a chamber which is filled with the mixture. This reduces separation of the $Mn_2O_3$ powder and the binder particles.

Preferably, the $Mn_2O_3$ powder has a purity of at least 98%, or at least 99%.

It may be that the ozone filter comprises a solid layer, the solid layer comprising $Mn_2O_3$. The ozone filter may comprise both said $Mn_2O_3$ powder (e.g. located in a chamber) and a solid layer, the solid layer comprising $Mn_2O_3$. The solid layer is typically a solid microporous layer comprising $Mn_2O_3$.

The solid microporous layer may be formed on a gas porous support, for example on a side facing the sensing electrode or a side facing away from the sensing electrode. It may be that the solid microporous layer is formed on a gas porous support which also supports the sensing electrode, e.g. on opposite sides.

The solid microporous layer may be formed only of $Mn_2O_3$. The solid microporous layer may comprise at least 50% or at least 75% or at least 85% of by mass $Mn_2O_3$. The solid microporous layer may comprise binder, for example PTFE (e.g. PTFE particles). It may be that at least 90% or at least 95% of the solid microporous layer is $Mn_2O_3$ mixed with binder. The solid microporous layer may for example comprise at least 5% of binder by mass or at least 10% of binder by mass. The solid microporous layer may for example comprise less than 25% of binder by mass or less than 15% of binder by mass.

Typically, the $Mn_2O_3$ in the solid microporous layer has a purity of at least 98%, or at least 99%. The $Mn_2O_3$ in the solid layer may be $NO_2$ treated as above. The solid layer may be formed from $Mn_2O_3$ powder which has been $NO_2$ treated as above.

It may be that the sensing electrode (and optionally the second sensing electrode, where present) is a carbon electrode. Carbon electrodes are advantageous in that $NO_2$ is reducible to give a current but interference from $SO_2$, CO, NO, $NH_3$ and $H_2$ is generally inhibited. The sensing electrode may however be another type of electrode, for example the (first) sensing electrode may comprise gold (for example it may be a gold or binary gold/gold oxide electrode). In the case of sensing $SO_2$, for example, the sensing electrode may be a gold and ruthenium electrode.

In some embodiments the said sensing electrode is a first sensing electrode and there is further provided a second sensing electrode. Typically, ozone is filtered from the sample gas received by the first sensing electrode by the ozone filter but ozone is not filtered from the sample gas received by the second sensing electrode. Thus, it may be that the gas sensing apparatus comprises a second sensing electrode, wherein the second sensing electrode is in gaseous communication with a gas sample (typically surrounding air) without an intervening ozone filter.

The second sensing electrode is used to obtain a measurement including a signal due to any ozone which is present in a gas sample. This signal can be compared with the signal from the first sensing electrode (which is in contact with gas which has been filtered by the ozone filter). The first sensing electrode and the second sensing electrode may be provided in separate electrochemical sensors. The electrochemical sensors may both be provided in the said housing. However, the second sensing electrode may be provided in a separate sensor body.

According to a second aspect of the invention there is provided a method of forming an electrochemical gas sensing apparatus for sensing at least one gaseous analyte, the method comprising providing a housing having an inlet and a sensing electrode and providing an ozone filter interposed between the sensing electrode and the inlet, wherein the ozone filter comprises $Mn_2O_3$.

Thus, the sensing electrode is in gaseous communication with a gas sample, typically surrounding gas (e.g. the surrounding atmosphere) through the ozone filter.

The at least one gaseous analyte may comprise or be $NO_2$ and/or ozone. The gaseous analyte may be $SO_2$.

The ozone filter may comprise $Mn_2O_3$ powder. The method of forming an electrochemical gas sensing apparatus may comprise the step of treating the $Mn_2O_3$ (e.g. $Mn_2O_3$ powder) with $NO_2$.

As a result, $NO_2$ adsorbs to the surface of the $Mn_2O_3$ (e.g. $Mn_2O_3$ powder). The $Mn_2O_3$ (e.g. $Mn_2O_3$ powder) is preferably treated with $NO_2$ until the $Mn_2O_3$ (e.g. $Mn_2O_3$ powder) is saturated with $NO_2$, i.e. until further treatment with $NO_2$ does not have a significant effect. It may be that the $Mn_2O_3$ (e.g. $Mn_2O_3$ powder) is treated with $NO_2$ at a concentration of at least 10 ppm for at least 30 mins. It may be that at least $10^{12}$, or at least $2 \times 10^{12}$ molecules of $NO_2$ are adsorbed per cm² of surface of $Mn_2O_3$. It may be that sufficient $NO_2$ is provided that at least 1 or at least 1.5 moles of $NO_2$ are adsorbed per gram of $Mn_2O_3$.

It may be that the $Mn_2O_3$ powder is mixed with binder particles. The filter may thereby comprise a mixture of $Mn_2O_3$ powder and binder particles. The $Mn_2O_3$ powder may coat the binder particles. In embodiments where the $Mn_2O_3$ is treated with $NO_2$, the treatment with $NO_2$ typically takes place after the $Mn_2O_3$ powder is mixed with binder, but this is not essential.

It may be that the ozone filter comprises a solid microporous layer, the solid microporous layer comprising $Mn_2O_3$. The ozone filter may comprise both said $Mn_2O_3$ powder (e.g. located in a chamber) and a solid microporous layer, the solid microporous layer comprising $Mn_2O_3$. The method may comprise gas passing through both a region of the ozone filter comprising $Mn_2O_3$ powder and a region of the ozone filter comprising a solid microporous layer, the solid microporous layer comprising $Mn_2O_3$ powder (optionally in that order) to reach the sensing electrode.

The solid microporous layer may be formed only of $Mn_2O_3$. The solid microporous layer may comprise binder, for example PTFE (e.g. PTFE particles). The solid microporous layer may for example comprise at least 5% of binder by mass or at least 10% of binder by mass. The solid microporous layer may for example comprise less than 25% of binder by mass or less than 15% of binder by mass.

The solid layer may comprise $Mn_2O_3$ which has been treated with $NO_2$ as above. The solid layer may be formed from $Mn_2O_3$ powder which has been $NO_2$ treated as above, optionally after mixing with one or more other components, for example binder (such as PTFE).

The solid microporous layer may be formed by compressing $Mn_2O_3$ powder (optionally after treatment with $NO_2$ as above and/or mixing with binder).

The method may comprise providing a second sensing electrode in gaseous communication with a gas sample (typically surrounding air) without an intervening ozone filter. The signals from the (first) and second sensing electrodes may be compared to measure the concentration of ozone or to cancel out the effect of ozone on the measurement of another gas (e.g. $NO_2$ or $SO_2$).

The first (and second, if present) sensing electrodes may for example be carbon electrodes or electrodes comprising gold (e.g. gold/gold oxide electrodes).

The invention extends to a method of sensing at least one gaseous analyte (for example, $NO_2$ and/or ozone, or $SO_2$ and/or ozone) comprising forming electrochemical gas sensing apparatus according to any one of claims 1 to 7, or by the method of any one of claims 8 to 12 and bringing the inlet into gaseous communication with a gas sample.

The gas sample may be ambient air around the gas sensing apparatus.

Thus, the invention extends to a method of sensing a gaseous analyte (for example $NO_2$ and/or ozone, or $NO_2$ and/or ozone) comprising forming an electrochemical gas sensing apparatus by the method set out above and bringing the apparatus into gaseous communication with a gas sample (e.g. the surrounding air) such that both the first and second sensing electrodes reduce any of a gaseous species (e.g. $NO_2$ or $SO_2$) in the gas sample, where present, and the ozone filter removes ozone, where present, from sample gas reaching the first sensing electrode but not the second sensing electrode, such that the difference in the signals (typically currents) in the first and second sensing electrodes is representative of the concentration of ozone in the gas sample, and thereby determining from the signals (typically currents) from the first and second sensing electrodes the concentration of $NO_2$ and/or ozone in the gas sample. This may also be applied to the detection of another gas (e.g. $SO_2$) and/or ozone.

The method may comprise sensing $NO_2$ and/or ozone in a gas sample which comprises a higher concentration of NO than $NO_2$. In this case, a low cross sensitivity to NO is of particular importance.

By a carbon electrode we refer to an electrode containing carbon as an electrode active material. Where the (first) sensing electrode (and second sensing electrode, where present) are carbon electrodes, the carbon of the (or each) carbon electrode may be activated carbon, amorphous carbon, graphite, graphene (the graphene may be in functionalised form, such as COOH-functionalised), glassy (or vitreous) carbon, fullerene, carbon nanotubes (including single walled, double walled and multi-walled carbon nanotubes) or boron-doped diamond (BDD) or some other suitable allotrope of carbon. It may be that the carbon of the (or each) carbon electrode is in the form of graphite, graphene, carbon nanotubes or glassy carbon. In one embodiment the carbon is graphite. In one embodiment, the carbon is chosen from single walled or double walled carbon nanotubes. In one embodiment, carbon is the only electrode active material in the electrode. In one embodiment, carbon is the main electrode active material in the electrode, i.e. over 50 weight %, preferably over 80 weight % of the total electrode active material present in the each of the first and second sensing electrodes is carbon. It may be that the first sensing electrode and the second sensing electrode (where present) comprise the same type of carbon. In this case, they may be the same in dimension and amount of electrode active material, so that each of the first sensing electrode and the second sensing electrodes provides a similar electrochemical response to $NO_2$. Alternatively the second sensing electrode (where present) can be made from a different type of carbon or have a different composition of electrode active material to that of the first sensing electrode.

In the embodiments with first and second sensing electrodes, the second sensing electrode may be an electrode at which both a first gas (e.g. $NO_2$) and $O_3$ are reducible. By this is meant that the first gas (e.g. $NO_2$) and $O_3$ can be reduced at the electrode. Thus, in operation, any of the first gas (e.g. $NO_2$) or $O_3$ reaching the second sensing electrode of the gas sensing apparatus of the invention will react to generate a current. In this case, the first sensing electrode is an electrode at which first gas (e.g. $NO_2$) is reducible. $O_3$ may also be reducible at this electrode. However, any significant amount of ozone in the sample gas would be filtered out by the ozone filter. Where the sensing apparatus is for sensing $NO_2$ and/or $O_3$ and the first and second sensing electrodes are carbon electrodes, we have found that carbon electrodes are very specific to $NO_2$ and $O_3$ and have low cross-sensitivities for other gases, i.e. $NO_2$ and $O_3$ will oxidise at the electrodes generating current reading whereas other gases such as NO and $SO_2$ will not. The use of such electrodes ensures a high level of accuracy of the measurement in the gas sensing apparatus of the invention. This is particularly important for the measurement of $NO_2$. Thus the gas sensing apparatus of the invention can be used to provide a highly accurate measurement of the amount of $NO_2$ in the atmosphere, for example in urban areas where the amount of $NO_2$ in the atmosphere is regulated by law. The ability of the gas sensing apparatus of the invention to make a highly accurate measurement of ozone (the amount of which in the atmosphere is also regulated by law) at the same time makes the apparatus a very versatile environmental monitoring instrument. This, the apparatus may be for the detection of the amount of $NO_2$ and $O_3$ (or for example $SO_2$ and $O_3$) in a sample gas, such as air, and is particularly useful in applications where an accurate determination is essential for health and safety reasons. In particular, the method of the invention provides a very accurate indication of $NO_2$.

In embodiments with first and second sensing electrodes, the gas sensing apparatus is configured so that, in operation, the second sensing electrode is exposed to the sample gas in parallel with the ozone filter. In other words, the second sensing electrode and the first sensing electrode are effectively exposed to the sample gas at the same time, the first sensing electrode being exposed to the sample gas after it has passed through the ozone filter. The ozone filter is configured and positioned such that it does not cause a significant delay in the transport of the sample gas to the first sensing electrode. The second sensing electrode and the ozone filter can be described as being simultaneously in direct communication with the sample gas, i.e. the second sensing electrode and the ozone filter are not exposed to the sample gas in series. This can be achieved by having the first and second sensing electrodes positioned in close proximity or adjacent to each other. By close proximity is meant that they are both present in the same 0.5 cm³ or between 1 and 5 mm apart, for example. The gas sensing apparatus of the invention can thus be small in size and compact.

The gas sensing apparatus of the invention is an electrochemical gas sensing apparatus and may, for example, be an amperometric gas sensing apparatus. The (first) sensing electrode (and the second sensing electrode, if present) may be working electrodes (of an amperometric sensor). In such apparatus each working electrode is associated with a counter electrode, a reference electrode and an electrolyte, i.e. the working electrode is connected conductively (electrochemically) to the counter electrode and reference electrode through the electrolyte. The counter electrode, reference electrode and electrolyte can be the same or different for each working electrode. A reduction or oxidation reaction at a working electrode generates a current between it and its counter electrode. The principle of amperometry is based on the measurement of this current. The reference electrode is used to set the operating potential of the working electrode or to bias the working electrode for best performance. The gas sensing apparatus can comprise a potentiostat circuit for this purpose. The gas sensing apparatus is preferably diffusion limited, with a diffusion barrier (such as a capillary or a porous membrane) controlling access of the sample gas to the working electrodes. The combination of electrodes operating should, in principle, have sufficient activity to maintain capillary diffusion limited behaviour. In other words the electrodes must be capable of fully consuming the capillary-limited flux of the target gas reaching it.

In some embodiments, the first and second working electrodes do not share common counter and reference electrodes, or a common electrolyte. Each of the first and second electrodes is associated with its own counter electrode, reference electrode and electrolyte. In this embodiment the gas sensing apparatus of the first aspect of the invention further comprises a first counter electrode, a first reference electrode, a first body of electrolyte and a second counter electrode, a second reference electrode and a second body of electrolyte. In this embodiment, each of first working, counter and reference electrodes are in electrochemical contact with each other through the first body of electrolyte and each of second working, counter and reference electrodes are in electrochemical contact with each other through the second body of electrolyte. In this embodiment of the invention, the gas sensing apparatus can comprise two individual gas sensors, one of which has first working, reference and counter electrodes and a first electrolyte, the other having second working, reference and counter electrodes, a second electrolyte and an ozone filter adjacent the first working electrode. The sensors can be identical, except for the presence of the ozone filter in one of them. The sensors can be situated and coupled to each other on the same circuit board.

In one embodiment, the first and second working electrodes are associated with and share a common counter electrode, a common reference electrode and a common electrolyte. In other words, the gas sensing apparatus of the first aspect of the invention further comprises one counter electrode, one reference electrode, and one body of electrolyte, with the first, second, counter and reference electrodes being in electrochemical contact with each other through said body of electrolyte. In this embodiment of the invention, a particularly compact gas sensing apparatus is achievable, due to the relatively small number of components.

The reference and counter electrodes used in the gas sensing apparatus of the invention can be made of various electrode active materials which include carbon, gold, gold alloys, Pt, and Pt alloys. The platinum can be in the form of platinum oxide which includes platinum black (Ptb) and the gold can be in the form of gold oxide which includes gold black. The carbon and a carbon electrode are as described above for the first and second working electrodes. The counter electrodes can be the same or different from the reference electrodes. In one embodiment, the first, second or common reference electrode is chosen from carbon, gold, gold alloy, Pt, and Pt alloy electrodes and the first second or common counter electrode is the same as or different from the respective first, second or common reference electrode. In one embodiment, the first, second or common reference electrode is chosen from carbon, gold, gold alloy, Pt, and Pt alloy electrodes and the first second or common counter electrode is a Ptb electrode. Other combinations of reference and counter electrodes include: carbon reference electrode and platinum black counter electrode; and gold reference electrode and platinum black or gold counter electrode.

In one embodiment, the working electrode, or each of the first and second working electrodes, where applicable, has an additional working electrode associated with it, the additional working electrode being incorporated in the gas sensing apparatus such that it is not exposed to the sample gas. The additional electrode is buried within the sensor body and is used to generate a signal for correcting the working electrode baseline for background signal drift due to, for example, temperature. This ability to correct the baseline signal of the working electrode for background drift means that the measurements of the gas sensing apparatus are highly accurate. This is particularly important when measuring low concentrations of $NO_2$ and $O_3$.

The additional working electrode can be made of various electrode active materials which include carbon, gold, gold alloys, Pt alloys and platinum. The platinum can be in the form of platinum oxide which includes platinum black (Ptb) and the gold can be in the form of gold oxide which includes gold black. The carbon and a carbon electrode are as described above for the first and second working electrodes. In one embodiment, the additional working electrode is a carbon electrode.

The electrolyte is typically a liquid electrolyte, for example, diluted $H_2SO_4$ (5M). Other standard electrolytes used in amperometric sensors include diluted $H_3PO_4$ and tetraalkyl ammonium salts dissolved in propylene carbonate. Typically, the first electrolyte, second electrolyte or a common electrolyte (as appropriate) are chosen from $H_2SO_4$, propylene carbonate and tetraethylammonium fluoride or $H_3PO_4$.

The apparatus of the invention can contain control circuits that can switch or activate/deactivate the electrodes and/or a processor for processing the current signals from the electrodes to thereby determine a concentration of the at least one analyte (e.g. $NO_2$ and/or $O_3$).

The optional features described above in respect of any aspect of the invention apply to each aspect of the invention, including both the product and process features.

DETAILED DESCRIPTION OF EXAMPLE EMBODIMENTS

Figure 1:
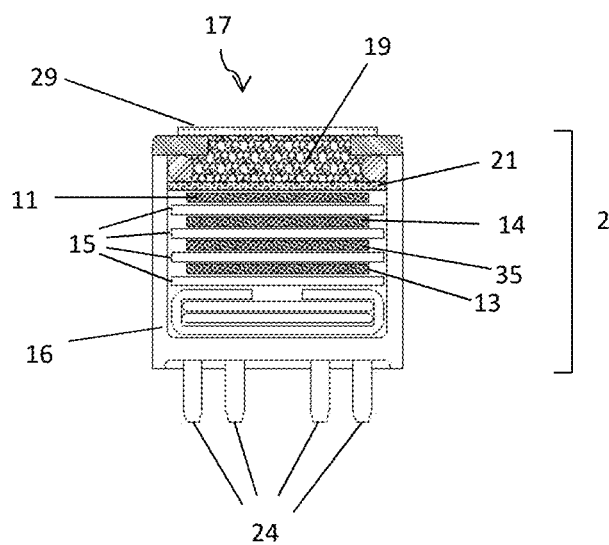
FIG. 1 relates to a gas sensing apparatus of the invention comprising a single electromechanical amperometric gas sensor for detecting $NO_2$, having an ozone filter, working electrode and its associated counter electrode, reference electrode, electrolyte and additional working electrode.

FIG. 1 is a schematic cross-sectional view of gas sensing apparatus according to the invention in the form of a gas sensor (2) having a housing (16), a (single) sensing working electrode (11), a counter electrode (13), a reference electrode (14), an additional working electrode (35) for correcting for baseline drift, and a body or reservoir of electrolyte, mainly held in wetting filters (15). The housing has an inlet (17) through which the working electrode (11) is placed in communication with a sample gas (e.g. the atmosphere), through an ozone filter (19).

A series of circular separator discs, wicks or wetting filters (15) separate the working electrode from the counter electrode and the reference electrode. The circular separator discs, wicks or wetting filters (15) are made of a hydrophilic, non-conductive material permeable to the electrolyte which functions to transport electrolyte by capillary action. Typically the material is glass fibre. The circular separator discs, wicks or wetting filters serve to ensure that each of the electrodes is in contact with the electrolyte.

The working electrode (11) is a carbon electrode and typically comprise a catalytic layer of carbon mixed with polytetrafluoroethylene (PTFE) binder which is then bonded to a gas porous, but hydrophobic, PTFE support to allow gas support to the catalyst, i.e. the electrode active material, but avoid electrolyte leakage or flooding of the electrode. The carbon electrodes can be manufactured using common conventional technologies such as pressing, screen printing, inkjetting and spraying a carbon slurry onto a porous membrane. Here the working electrode catalyst will typically have a diameter of 14 mm. A mixture of carbon and microparticulate polytetrafluoroethylene (PTFE) is sintered and is preferably prepared by pressing the resulting mixture onto a support in the form of a gas porous membrane, such as PTFE sheet. Where carbon is pressed at the normal pressure used in the field, i.e. around 200 kg/cm$^2$, the amount of catalyst is preferably between 5 and 30 mg per cm$^2$ of electrode surface area. Preferably the binder is a Fluon matrix (Fluon is a Trade Mark) of around 0.002 ml per cm$^2$. Other electrodes used in the gas sensing apparatus of the invention, such as the Platinum black electrodes can be prepared in a similar way.

An O ring is located at the top of the porous membrane (21) and acts to seal the sensor and to aid compressing the stack of components when the sensor is sealed. Also present are a number of platinum strips that serve to connect each electrode to one of the terminal pins (24) provided at the base of the sensor. Closing housing is a dust filter (29) to prevent dust and other foreign objects from entering.

The ozone filter (19) is formed of $MnO_2$ powder which has been treated with $NO_2$ as described below and the sensor is useful to sense $NO_2$ in the presence of gases such as $SO_2$, CO, NO, $NH_3$, $H_2$ and $O_3$, which were it not for the choice of electrode and the presence of the ozone filter, would otherwise interfere with the measurement.

Figure 2A:
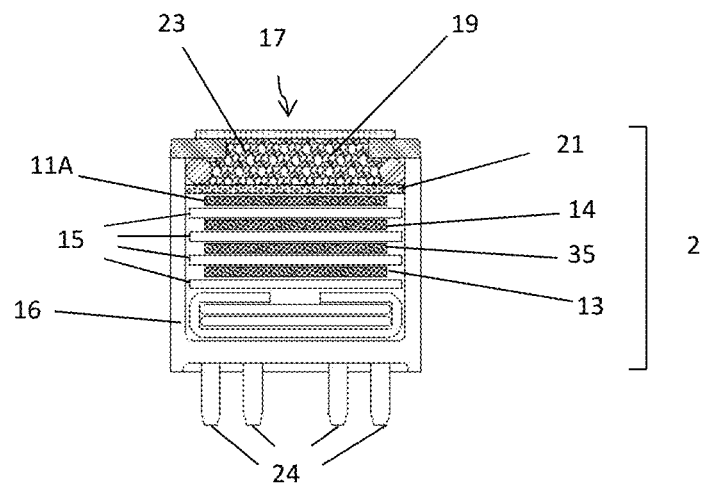
FIGS. 2A and 2B relates to a gas sensing apparatus of the invention according to an embodiment comprising two individual electrochemical amperometric gas sensors one (shown in FIG. 2A) housing an ozone filter, the first working electrode and its associated counter electrode, reference electrode, electrolyte and additional working electrode, the other (shown in FIG. 2B) housing another (the second) working electrode and its associated counter electrode, reference electrode, electrolyte and additional working electrode.
Figure 2B:
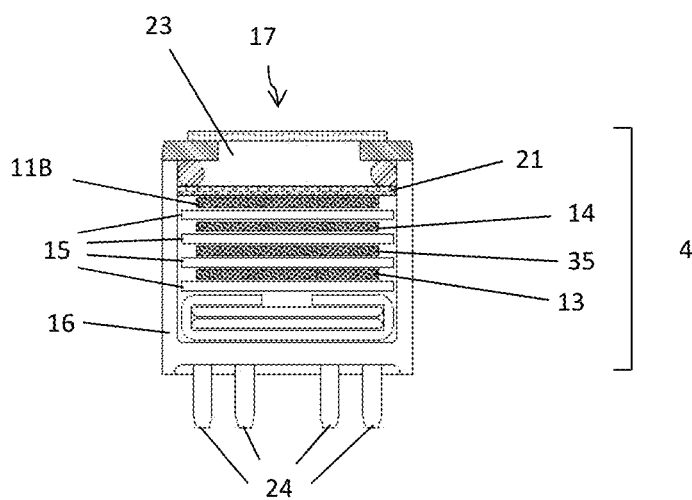

FIGS. 2A and 2B are together a schematic cross-sectional diagram of gas sensing apparatus according to the invention in the form of two individual gas sensors (2) (shown in FIG. 2A) and (4) (shown in FIG. 2B), each having its own housing (16), working electrode, counter electrode (13), reference electrode (14), additional electrode (35) and electrolyte held mainly in wetting filters (15). Together, these form a gas sensing apparatus according to the invention. These gas sensors have similar stacked structures.

The first gas sensor (2) has an ozone filter (19) in internal chamber (23) above the working electrode (11A), functioning as the first working electrode. Again, the ozone filter is prepared by the method set out below. The second gas sensor (4) has a working electrode (11B), which is the same as the working electrode (11A) of the first gas sensor (4) but functions as the second working electrode, and has no ozone filter in the internal chamber (23). The two working electrodes (11A), (11B) correspond to those described above in relation to FIG. 1.

The embodiment of FIGS. 2A and 2B is especially useful for detecting $NO_2$ in the presence of ozone, or for detecting ozone, or both. This is because ozone is removed from the sample gas which penetrates the inlet of the first gas sensor (2), before $NO_2$ is sensed by the working electrode, and so the first gas sensor gives a measurement of the concentration of $NO_2$ only, but ozone is not filtered from the gas received through the inlet of the second gas sensor (4) and so the second gas sensor gives a signal which is indicative of the concentration of both $NO_2$ and ozone. The two signals can therefore be processed to independently determine the concentration of $NO_2$ and ozone and therefore to measure either $NO_2$, or ozone, or both.

In some of the embodiments discussed below, the sensor of FIG. 2A is replaced with the sensor of FIG. 2C. The sensor of FIG. 2C corresponds to the sensor of FIG. 2A except that there is no filter powder received in the chamber (23) and instead there is an additional microporous PTFE membrane (25) having a microporous solid filter layer (27) comprising $Mn_2O_3$ formed thereon between the inlet (17) and the first working electrode (11A). The filter layer can be formed on the inward or outward surface of the membrane (25). In some embodiments, there is a Mn2O3 powder present in the chamber (23) in addition to the solid filter layer (27).

Figure 3:
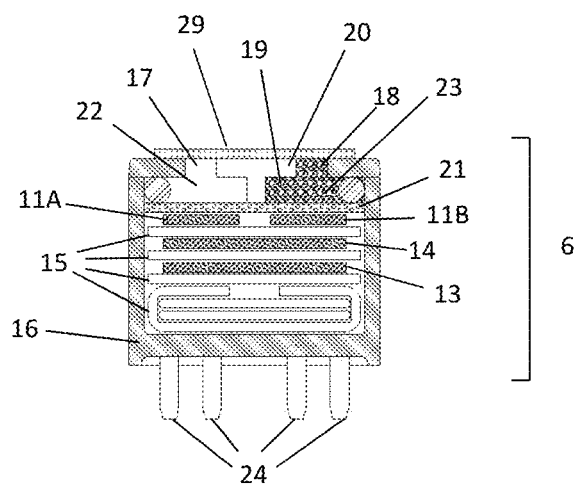
FIG. 3 is a schematic cross-sectional view of a gas sensing apparatus of the invention according to an embodiment wherein first and second working electrodes are combined into the same housing and share a common counter electrode, reference electrode and electrolyte.

FIG. 3 is a schematic cross-sectional view of a further embodiment of gas sensing apparatus (6) in which the first (11B) and second (11A) working electrodes share a common counter electrode (13), a common reference electrode (14) and a common body or reservoir of electrolyte, again mainly held in wetting filters (15). In this case, the housing (16) has two inlets (17) and (18), which place the second working electrode (11A) and the $O_3$ filter (19) in direct communication with the sample gas (e.g. the atmosphere) in parallel. Inlets (17) and (18) can be capillary inlets, i.e. inlets which are sized so that they control the rate of sample gas reaching the electrodes so that the gas sensing apparatus is diffusion limited. A central portion (20) divides a cavity defined by the housing (16) and a porous membrane (21) into first (22) and second (23) internal chambers. The first and second working electrodes are located in the same horizontal plane and are situated underneath the porous membrane (21). The second working electrode (11A) is situated underneath the first internal chamber (22) and the first working electrode (11B) is situated underneath the second internal chamber (23). The ozone filter (19) is located in the second internal chamber (23), adjacent/on top of part of the porous membrane (21) covering the first working electrode (11B). The ozone filter (19) covers the surface of the first working electrode (11B) that would, absent the filter, be exposed to the sample gas.

Figure 4:
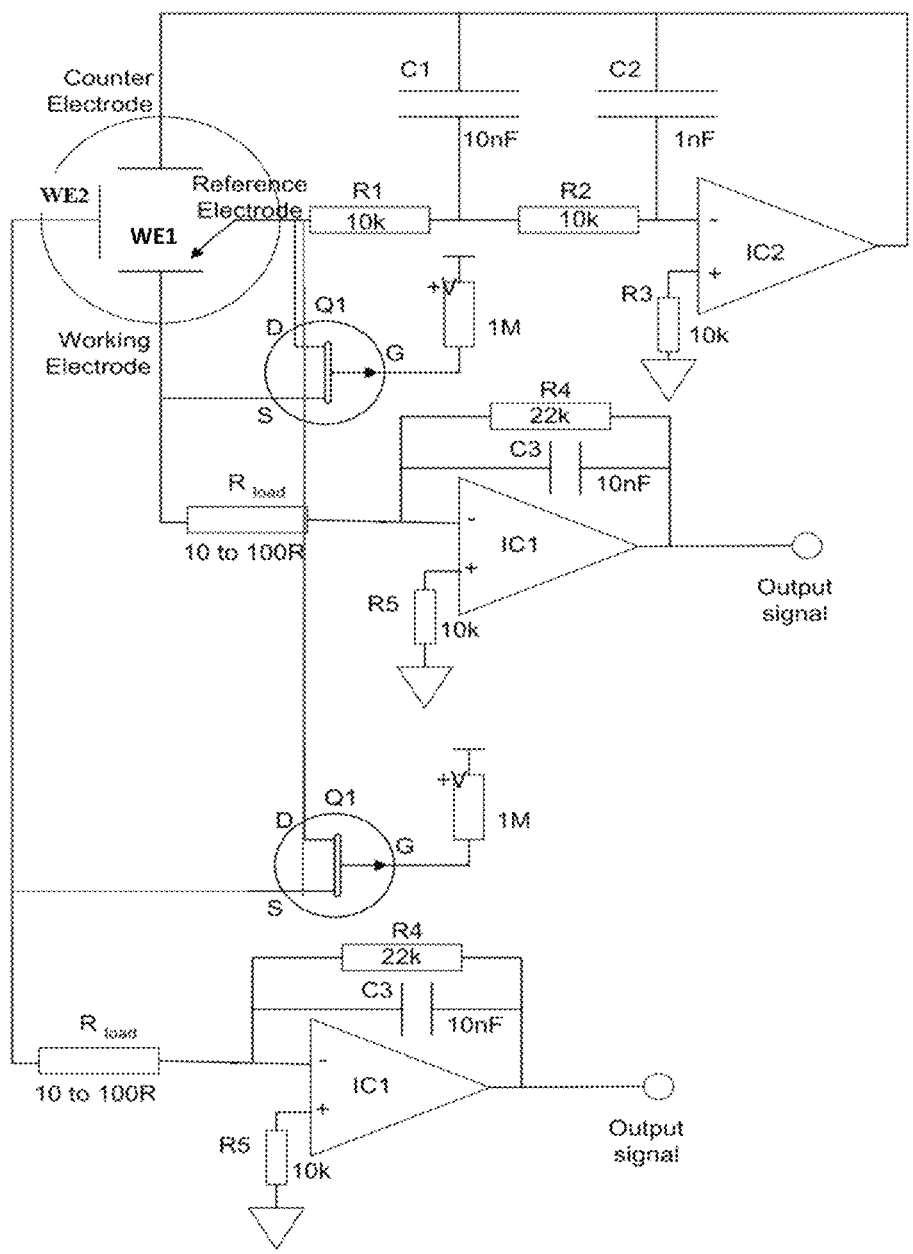
FIG. 4 is a diagram of potentiostatic circuitry for a gas sensing apparatus in which first and second working electrodes share a common counter electrode, reference electrode and electrolyte as for example, in the embodiment of FIG. 1 or in which a working electrode and an additional working electrode share a common counter electrode, reference electrode and electrolyte as for example, in one of the individual gas sensors of the embodiment of FIG. 2.

Example circuitry for the gas sensing apparatus of the invention in the embodiment of FIG. 3 is shown in FIG. 4, where WE1 is the second working electrode (11A) and WE2 is the first working electrode (11B). This circuitry could also be used for either of the individual sensors making up the gas sensing apparatus of the invention in the embodiment of FIG. 2, where, for example, WE1 is the second working electrode and WE2 is the first additional working electrode, or WE1 is the first working electrode and WE2 is the second additional working electrode. It could also be used for a simple individual sensor according to FIG. 2A (or 2B) but lacking an additional working electrode in which case WE1 is the working electrode and is the only one recorded.

Forming the Ozone Filter

Figure 5:
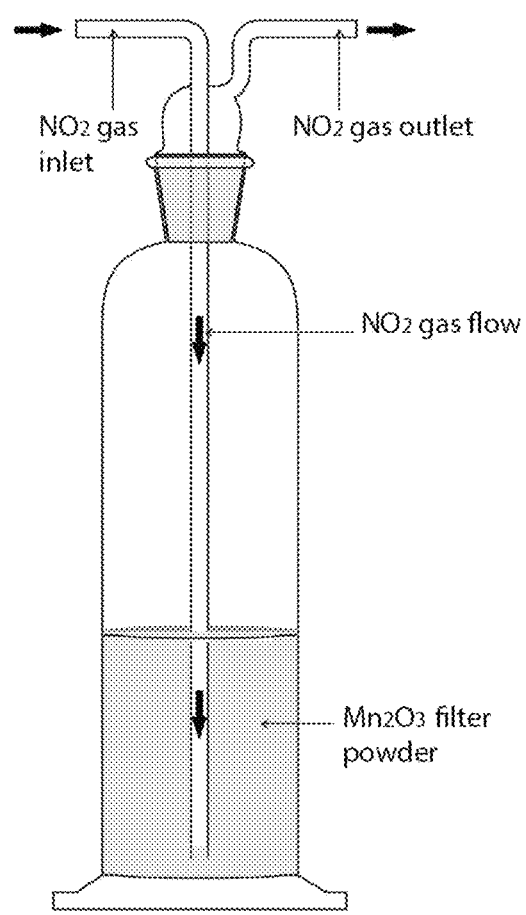
FIG. 5 is an illustration of the experimental setup used for the treatment of the $Mn_2O_3$ filter powder.

In order to form the ozone filter, $Mn_2O_3$ filter powder (99% purity) is treated by passing a flow of $NO_2$ gas therethrough. With reference to FIG. 5, the $Mn_2O_3$ filter powder is inserted into a gas washing bottle (or Drechsel's bottle) which is then connected through the inlet to a source of $NO_2$ gas. The $Mn_2O_3$ may first be also be mixed with PTFE powder, acting as binder.

In an illustrative example, 20 g of $Mn_2O_3$ or 30 g or 50 g of $Mn_2O_3$/PTFE filter powder was treated in a 250 ml gas washing bottle. The $NO_2$ gas was passed through the filter powder at a concentration of 100 ppm and a flow rate of 0.5 l·min$^{-1}$ for 2 hours.

By monitoring the concentration of $NO_2$ gas leaving the bottle, we therefore calculated the amount of $NO_2$ which was adsorbed before the $Mn_2O_3$ was saturated. This experiment was repeated. It was found that 1.78×10−8 moles of $NO_2$ were adsorbed per gram of $Mn_2O_3$. Using the value of surface area of the $Mn_2O_3$ powder obtained from BET analysis of 2.42 m2/g we estimated that 2.41×1012 molecules of $NO_2$ were adsorbed per cm2 of $Mn_2O_3$ surface. This is consistent with the values repeated in the paper J. Phys. Chem. C 2014, 118, 23011-23021 where the number of $NO_2$ molecules adsorbed on TiO2 are in the order of 1013 molecules/cm2.

Figure 13:
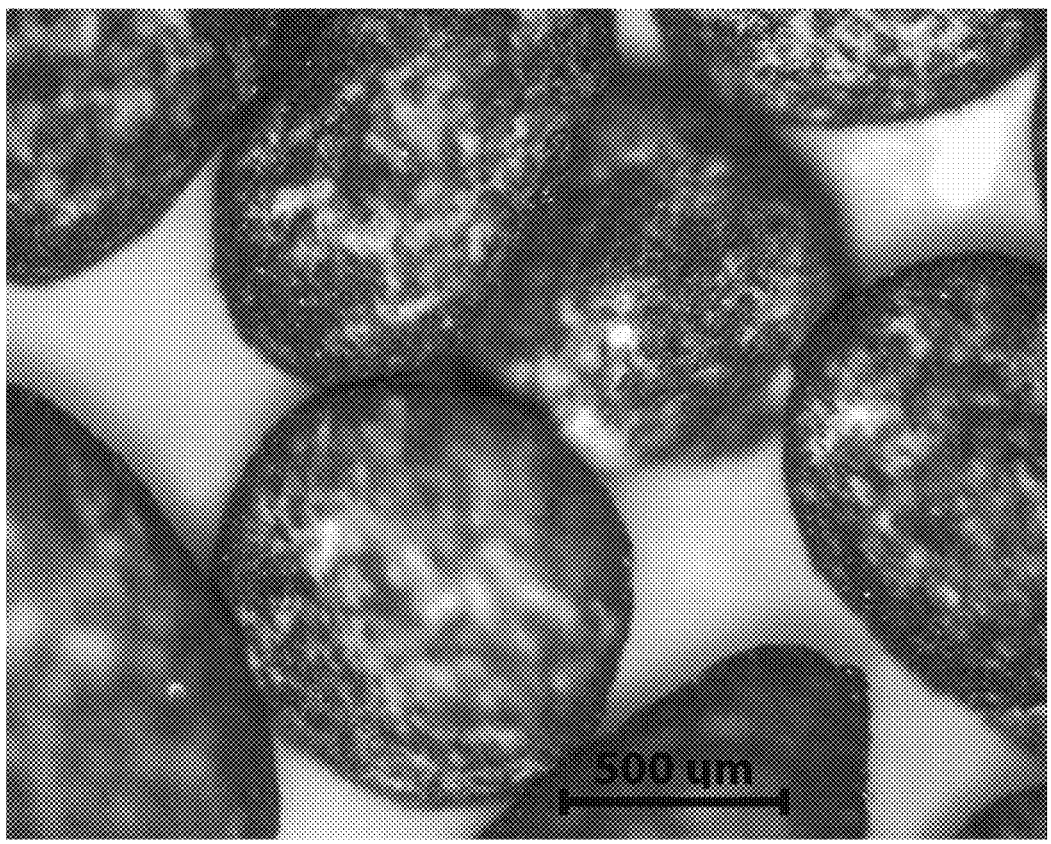
FIG. 13 is a photograph, to the scale shown, of filter material according to the invention, in the form of PTFE particles coated with $Mn_2O_3$ crystals.

The resulting material is advantageous in that it filters ozone with minimal degradation of the $NO_2$ signal compared to untreated $Mn_2O_3$. The layer remains gas permeable. Furthermore, it filters ozone efficiently, enabling a relatively low proportion of $Mn_2O_3$ mixed with PTFE to function effectively, reducing cost. An image of the resulting $Mn_2O_3$ coated PTFE particles is shown in FIG. 13.

A mixture of $Mn_2O_3$ and PTFE particles having a size of having a size range of 710 μm to 1500 μm was prepared by manually mixing $Mn_2O_3$ powder with PTFE in a glass container until all $Mn_2O_3$ powder coats the PTFE. In some of the examples below, $Mn_2O_3$ and PTFE were mixed in a weight ratio of 1:10. The resultant mixture is then sieved through a 710 micron sieve stack using a motorised mechanical sieve for 1 hour. The portion that did not fall through the 710 micron sieve is then collected while the remaining material that did fall through the 710 micron sieve is discarded.

In some examples below, $Mn_2O_3$ and PTFE were also mixed in a weight ratio of 1.6:8.4 (16% by weight). In those examples, the resultant mixture was then sieved through a 500 micron sieve stack using a motorised mechanical sieve for 1 hour. The portion that did not fall through the 500 micron sieve was then collected while the remaining material that did fall through the 500 micron sieve was discarded.

In the examples where the $Mn_2O_3$ was mixed with 100 micron PTFE in a weight ratio of 1.6:8.4 (16% by weight), resultant mixture was then thoroughly shaken using a motorised mechanical sieve for 1 hour.

Filter in the Form of a Solid Layer of Powdered $Mn_2O_3$:

For examples 13 to 15, solid filter layers of powdered $Mn_2O_3$ were formed with a diameter of 14 mm and 19 mm. A mixture of powdered $Mn_2O_3$ and microparticulate polytetrafluoroethylene (PTFE) was sintered and the resulting mixture was pressed onto a support PTFE sheet, acting as a gas porous membrane. $Mn_2O_3$ was pressed at the normal pressure used in the field, i.e. around 400-600 kg/cm$^2$, and the amount of $Mn_2O_3$ was in the range 15 to 30 mg per cm$^2$ of surface area. The $Mn_2O_3$ was mixed with a Fluon matrix (Fluon is a Trade Mark) of around 0.0065 ml per cm$^2$, which contains PTFE which acted as binder. In these examples Fluon with a PTFE particle size in the range of 200-300 microns diameter was used. $Mn_2O_3$ was 74% by weight of the solid microporous layer, with the balance being PTFE.

EXPERIMENTAL SECTION

The sensors used in the following experiments were tested on standard potentiostatic circuit boards (FIG. 4). Generally, the sensors were stabilised for a minimum of 2 days before being tested. All the experiments involving gas tests were controlled using computer controlled valves and digital mass flow controllers. Sensor output data collection is also made using a computer. The $NO_2$ gas tests were made using a certified 100 ppm bottle (Air Products, UK) and filtered air, except that a 10 ppm bottle (Air Products, UK) was used for Experiment 2 and the linearity test of Experiment 7. The ozone was obtained using a calibrated ozone generator equipped with an internal analyser (Thermo Scientific, Model 49i-PS), except for Experiment 2 and the filter capacity test of Experiment 5 where the ozone was obtained using a calibrated ozone generator (Ultra-violet Products Ltd, SOG-1, Cambridge, UK). During the laboratory tests the sensors were exposed to a gas flow of 0.5 l·min$^{-1}$.—

The following materials were used in the filter powder. These materials were used in each following experiment unless indicated to the contrary.

Manganese (III) oxide ($Mn_2O_3$), 99% purity, approx. 325 mesh (44 micrometers) powder, from Sigma Aldrich, product number 377457. BET analysis on the sample gives a surface area of 2.242 m$^2$/g.

Manganese (IV) oxide ($MnO_2$), 99.9% purity, approx. 325 mesh (44 micrometers) powder, from Alpha Aesar, product number 42250. BET analysis on the sample gives a surface area of 2.08 m$^2$/g.

PTFE binder (Fluon PTFE G307 (median particle size 500 to 1500 microns) (Fluon is a trade mark). The powder was sieved to collect only particles with a size of at least 710 microns. Also: Fluon PTFE G201 (median particle size 500 microns) and Fluon PTFE G204 (median particle size 100 microns).

The working electrodes were made from carbon graphite (particle size <20 μm, Aldrich, product code 282863).

Calibration of the sensors according to the invention was carried out as follows. The sensor output is given in nA. Amperometric gas sensors have a linear output with target gas analyte concentration. This makes possible to use a simple calibration procedure where the relation between the sensor output and the gas concentration is determined by exposing the sensor to a known concentration of gas analyte. For this application the sensitivity to both the first and the first working electrodes is determined for each of the target gases, $NO_2$ and $O_3$. The sensor output can then be used to calculate the concentration of $NO_2$ and $O_3$.

If the following parameters are defined as follows:
$i_1$ is the current observed on the second working electrode.
$I_2$ is the current observed on the first working electrode.
$S_{1(NO2)}$ is the second working electrode sensitivity to $NO_2$.
$S_{1(O3)}$ is the second working electrode sensitivity to $O_3$.
$S_{2(NO2)}$ is the first working electrode sensitivity to $NO_2$.
$S_{2(O3)}$ is the first working electrode sensitivity to $O_3$.
$C_{(NO2)}$ is the $NO_2$ analyte concentration to determine.
$C_{(O3)}$ is the $O_3$ analyte concentration to determine.

Then, by definition and taking into account the linear relationship between the sensor output and the analyte concentration, the following can be written:

$$i_1 = S_{1(NO2)} \cdot C_{(NO2)} + S_{1(O3)} \cdot C_{(O3)}$$

$$i_2 = S_{2(NO2)} \cdot C_{(NO2)} + S_{2(O3)} \cdot C_{(O3)}$$

The ozone filter on top of the first working electrode means that $S_{2(O3)}=0$. So $C_{(NO2)}$ can be calculated using the simple relation:

$$C_{(NO2)}=i_2/S_{2(NO2)}$$

The $NO_2$ analyte concentration being now known it is then possible to calculate the $O_3$ analyte concentration using the second working electrode output:

$$C_{(O3)}=(i_1-S_{1(NO2)}\cdot C_{(NO2)})/S_{1(O3)}$$

or $C_{(O3)}=(i_1-S_{1(NO2)}\cdot(i_2/S_{2(NO2)}))/S_{1(O3)}$

Experiment 1

In a first example, sensors according to FIG. 2A (filtered) were formed with $Mn_2O_3$, 99% purity (without PTFE) with and without the nitrogen dioxide pretreatment step described above. The response of these sensors and sensors according to FIG. 2B (i.e. unfiltered) to ozone and $NO_2$ was compared. The unfiltered sensor is commercially available under the trade name OX-A421, manufactured and sold by Alphasense Limited of Great Notley, United Kingdom.

For these and subsequent experiments the first working electrode, the second working electrode, the additional electrode and the reference electrode are made of carbon graphite and the counter electrode is made of platinum black.

Figure 6:
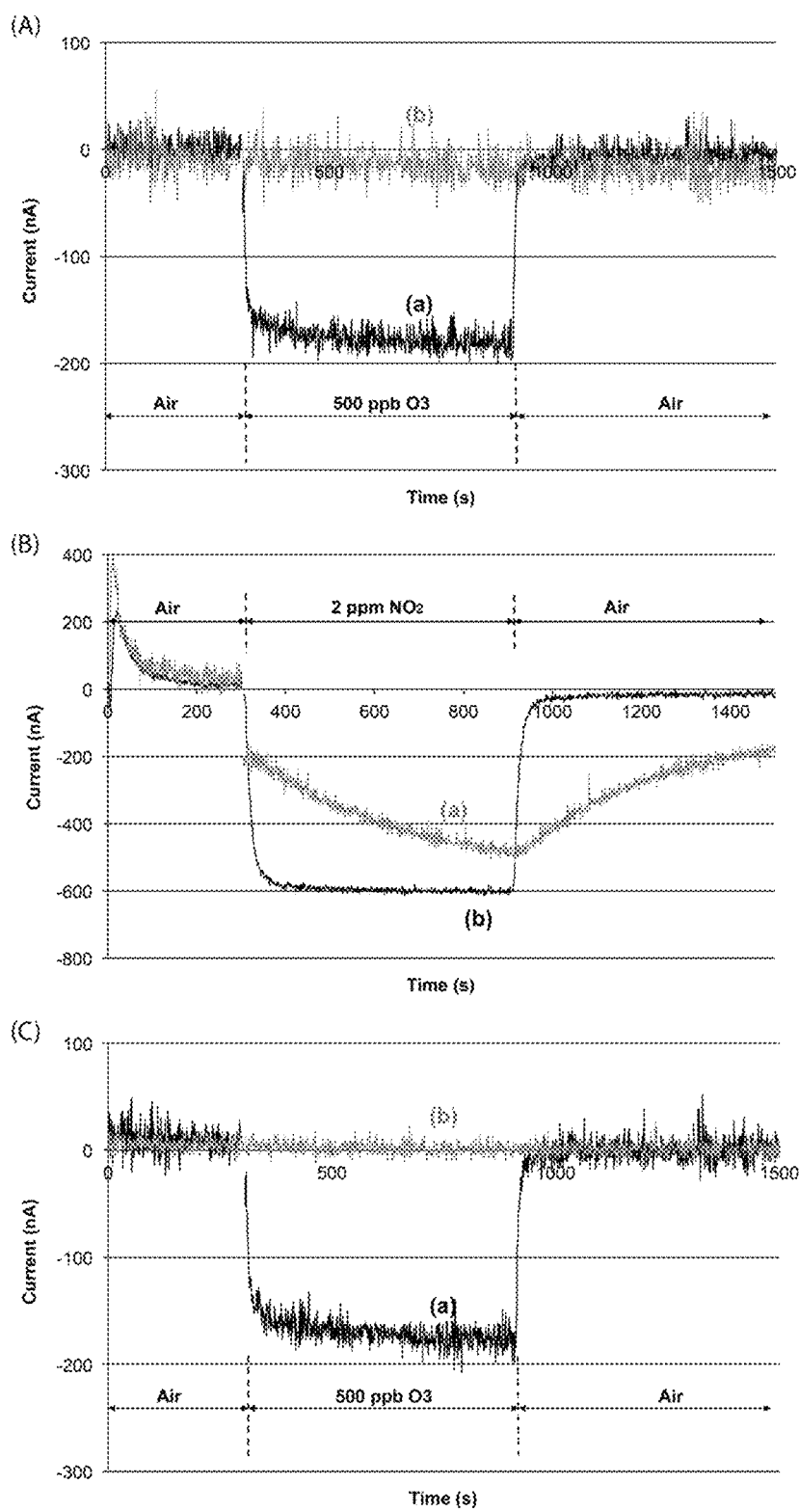
FIG. 6A shows the current response to 0.5 ppm $O_3$ of (a) unfiltered sensors according and (b) sensors in which the filter is 500 mg solid untreated $Mn_2O_3$.
FIG. 6B shows the current response to 2 ppm $NO_2$ of (a) a sensor in which the filter is 500 mg solid untreated $Mn_2O_3$ and (b) a sensor in which the filter is 500 mg of solid $Mn_2O_3$ treated with $NO_2$ as described above.
FIG. 6C shows the current response to 0.5 ppm $O_3$ of (a) unfiltered sensors and (b) sensors in which the filter is 500 mg solid $Mn_2O_3$ treated with $NO_2$ as described above.

FIG. 6A shows the current response to 0.5 ppm $O_3$ of (a) unfiltered sensors and (b) sensors in which the filter is 500 mg of untreated $Mn_2O_3$.

FIG. 6B shows the current response to 2 ppm $NO_2$ of (a) a sensor in which the filter is 500 mg of untreated $Mn_2O_3$ and (b) a sensor in which the filter is 500 mg of $Mn_2O_3$ treated with $NO_2$ as described above.

FIG. 6C shows the current response to 0.5 ppm $O_3$ of (a) unfiltered sensors and (b) sensors in which the filter is 500 mg of $Mn_2O_3$ treated with $NO_2$ as described above.

It is apparent from the results that the untreated $Mn_2O_3$ filter efficiently removes $O_3$. No signal is observed in the presence of 500 ppb of $O_3$ (FIG. 6A, curve (b)) but a sensor which differs only by the omission of the filter gives a clearly defined current response. However, it can be seen that the untreated filters added to the sensors to remove $O_3$ do affect the $NO_2$ signal. It is apparent from FIG. 6B, curve (a) that the resulting signal is not adequate for reliable sensing of $NO_2$. However, we have found that a well-defined signal for $NO_2$ can be obtained with the $NO_2$ pretreatment step set out above. It can be seen from FIG. 6C, curve (b), that the treated $Mn_2O_3$ remains effective for the filtering of $NO_2$.

Experiment 2

In this example, sensing apparatus comprised a sensor according to FIG. 2A in which the filter (59) in the chamber (52) was formed with 500 mg $Mn_2O_3$, (without PTFE), and a sensor according to FIG. 2B (unfiltered).

For this and all subsequent experiments, the $Mn_2O_3$ had been treated with $NO_2$ gas described above.

Figure 7:
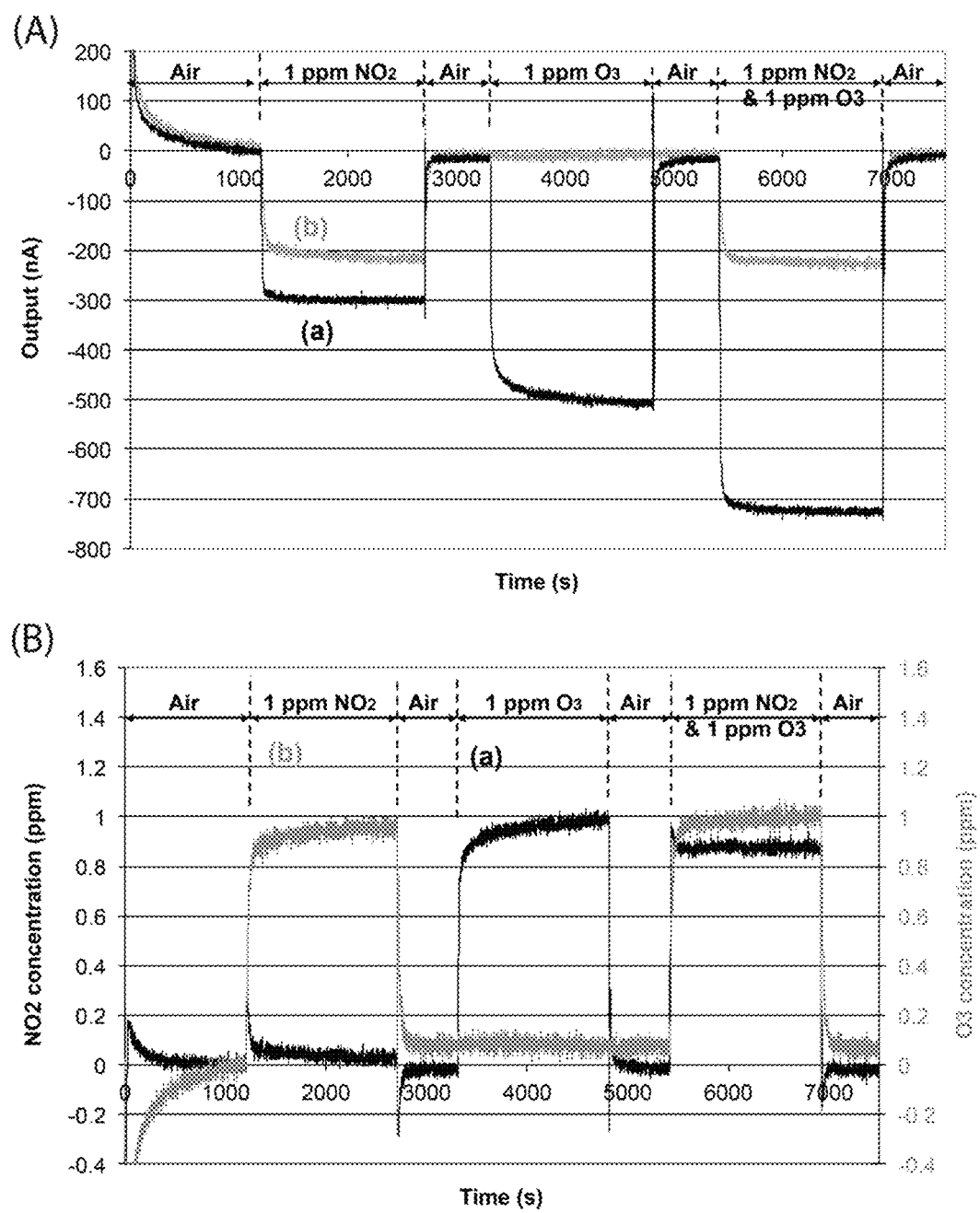
FIG. 7A illustrates the output current, over time, where the unfiltered sensor (trace (a)) and filtered sensor (trace (b)) are exposed in turn to zero air, then 1 ppm $NO_2$, then zero air, then 1 ppm $O_3$, then zero air, then a mixture of 1 ppm $NO_2$ and 1 ppm $O_3$.
FIG. 7B shows the calculated $O_3$ concentration (trace (a)) and $NO_2$ concentration (trace (b)) which the traces of FIG. 7A represents.

FIG. 7A illustrates the output current, over time, where the unfiltered sensor (trace (a)) and filtered sensor (trace (b)) are exposed in turn to zero air (zero air is air that has been filtered to remove most gases ($NO_2$, NO, CO, $SO_2$, $O_3$, etc.) and is used as a calibrating gas for zero concentration), then 1 ppm $NO_2$, then zero air, then 1 ppm $O_3$ and then zero air and then a mixture of 1 ppm $NO_2$ and 1 ppm $O_3$. FIG. 7B shows the calculated $O_3$ concentration (trace (a)) and $NO_2$ concentration (trace (b)) which these traces represent.

This figure shows that with a mixture of $NO_2$ and $O_3$, the filtered sensor senses only $NO_2$, whereas the unfiltered sensor detects both gases and, in the presence of both gases simultaneously, the output of the unfiltered sensor corresponds to the sum of the output expected for each of the gases. Accordingly, $Mn_2O_3$ is suitable as a filter material to remove ozone without affecting the signal due to $NO_2$.

Experiment 3

Figure 8:
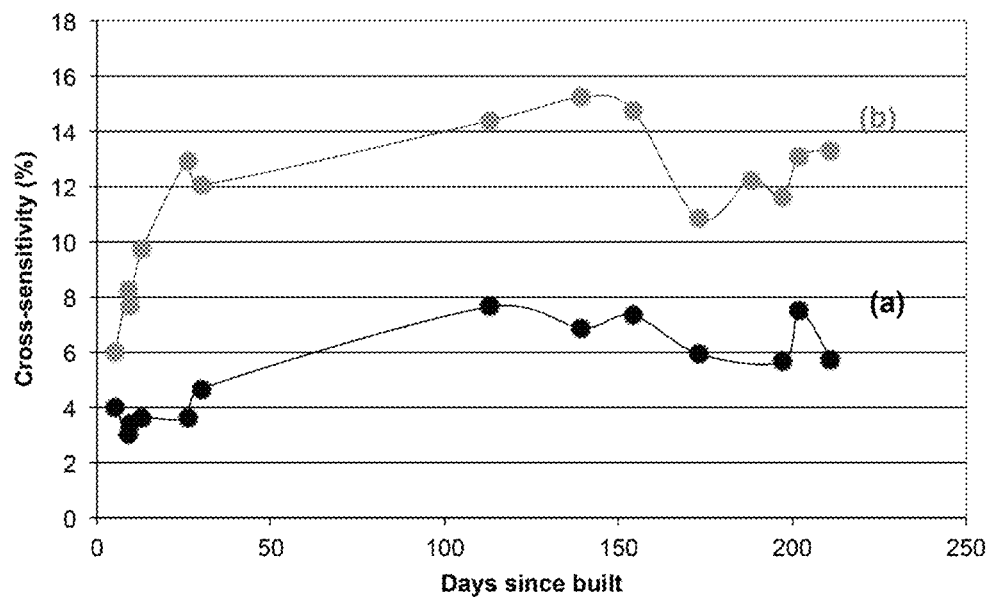
FIG. 8 is a plot of the variation with time in cross-sensitivity to NO (as a fraction of the sensitivity to $NO_2$) of (a) a sensor according to FIG. 2A(a) in which the filter is formed from 500 mg of solid $Mn_2O_3$, and (b) in which the filter is formed from 450 mg of solid $MnO_2$.

Sensors according to FIG. 2A (filtered) were formed with filters comprising (a) 500 mg of $Mn_2O_3$, and (b) 450 mg of $MnO_2$ were exposed to 2 ppm $NO_2$ for 10 minutes and then to 2 ppm nitrogen monoxide NO for 10 minutes. FIG. 8 is a plot of the variation with time in cross-sensitivity of the sensors (a) and (b) to NO, i.e. the current response to NO as a fraction of the current response to a corresponding concentration (in this case ppm) of $NO_2$.

This shows that the cross-sensitivity to NO is systematically lower with $Mn_2O_3$ than $MnO_2$, and that this improvement persists.

Experiment 4

Figure 9:
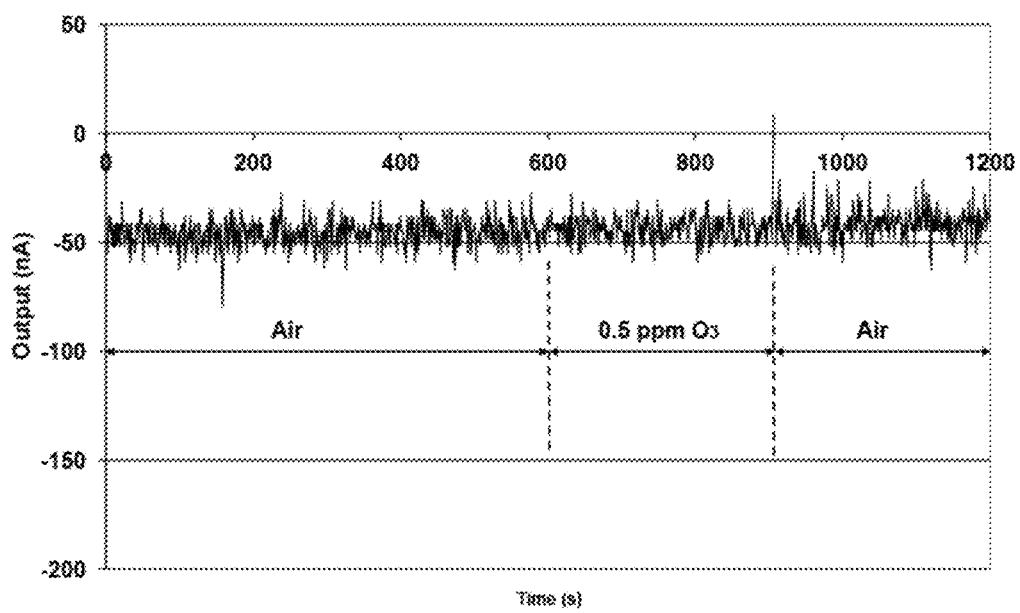
FIG. 9 shows the output current with time in the presence of zero air, then 0.5 ppm $O_3$, then zero air of sensors according to FIG. 2A (filtered) in which the filters were formed by 25 mg of powdered $Mn_2O_3$ mixed with 225 mg of PTFE particles having a size range of 710 µm to 1500 µm (i.e. 10% by weight of $Mn_2O_3$ in binder).

Sensors according to FIG. 2A (filtered) were formed with ozone filters comprising mg of powdered $Mn_2O_3$ mixed with 225 mg of PTFE particles having a size range of 710 μm to 1500 μm (i.e. 10% by weight of in $Mn_2O_3$ binder), and exposed to zero air, then 0.5 ppm $O_3$, then zero air. FIG. 9 shows the output current with time and demonstrates that ozone is efficiently filtered out by $Mn_2O_3$ mixed with PTFE binder (10% by weight of $Mn_2O_3$ in PTFE binder particles).

Experiment 5

Figure 10:
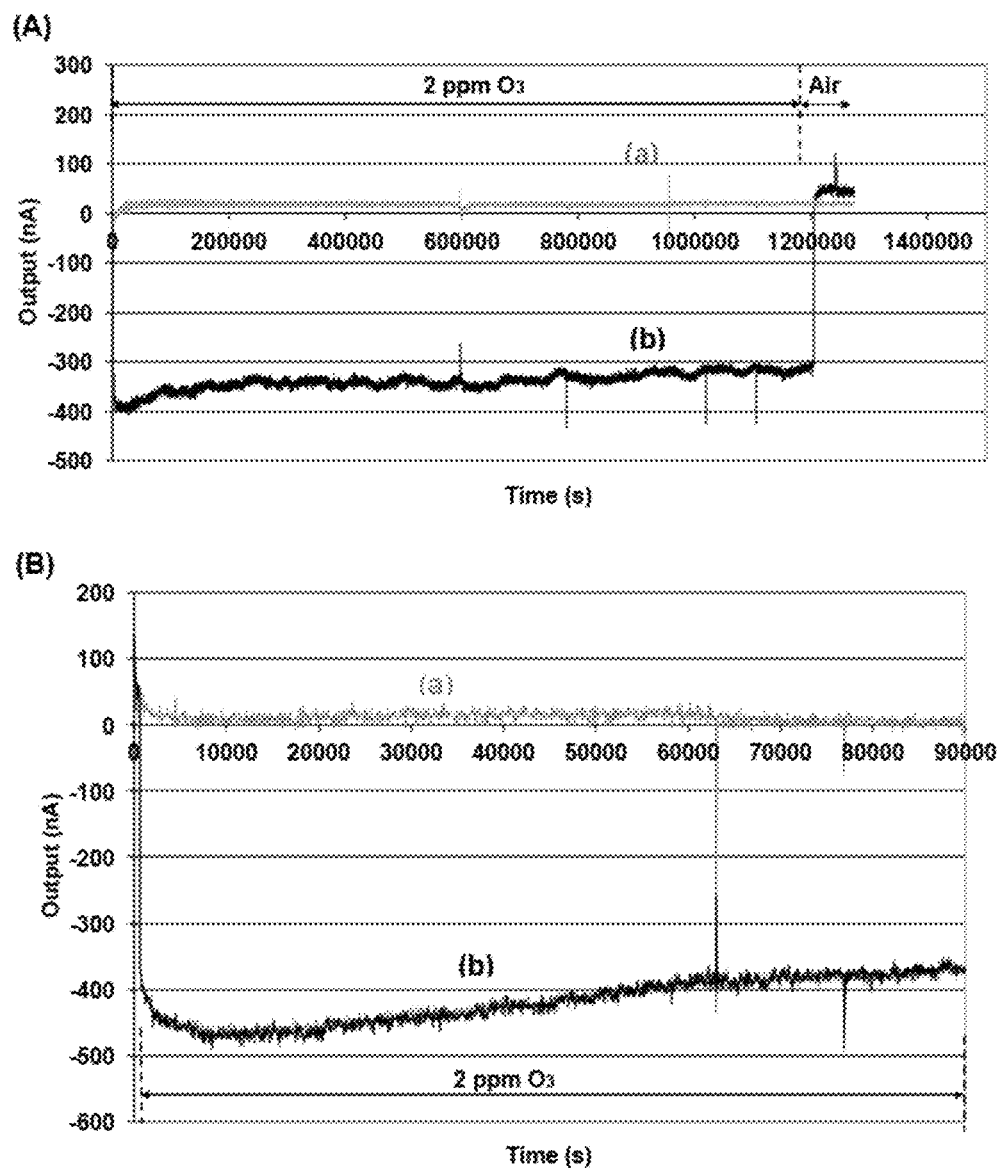
FIG. 10A shows the current response with time to 1 ppm of $O_3$ of (a) a sensor according to FIG. 2A (filtered) in which the ozone filter comprised 500 mg of powdered $Mn_2O_3$, (not mixed with binder) and (b) a sensor according to FIG. 2B (unfiltered), and in FIG. 10B (a) a sensor according to FIG. 2A (filtered) in which the ozone filter comprised 25 mg of powdered $Mn_2O_3$ mixed with 225 mg of PTFE particles having a size range of 710 µm to 1500 µm (i.e. 10% by weight of $Mn_2O_3$ in binder) and (b) a sensor according to FIG. 2B (unfiltered).

The ozone filtering capacity of the sensors was further tested and FIG. 10 shows the current response to 1 ppm of $O_3$ (2 ppm of $O_3$ is relatively high in comparison to levels typically measured in environmental monitoring) of in FIG. 10A (a) a sensor according to FIG. 2A (filtered) in which the ozone filter comprised 500 mg of powdered $Mn_2O_3$ (not mixed with binder) and (b) a sensor according to FIG. 2B (unfiltered), and in FIG. 10B (a) a sensor according to FIG. 2A (filtered) in which the ozone filter comprised 25 mg of powdered $Mn_2O_3$ mixed with 225 mg of PTFE particles having a size range of 710 μm to 1500 μm (i.e. 10% by weight of in $Mn_2O_3$ binder) and (b) a sensor according to FIG. 2B (unfiltered). In the case of FIG. 10A the experiment was continued for 14 days and in the case of FIG. 10B for 10 hours.

These results again demonstrate that $Mn_2O_3$ powder, whether unmixed or mixed with mg of PTFE particles having a size range of 710 μm to 1500 μm forms an efficient ozone filter.

Experiment 6

Experiments were carried out to assess the cross sensitivity of the sensors to common interferents. Table 1, below, shows the cross sensitivity of sensors formed with (a) mg of powdered $Mn_2O_3$ and (b) 25 mg of powdered $Mn_2O_3$ mixed with 225 mg of PTFE particles having a size range of 710 μm to 1500 μm (i.e. 10% by weight of $Mn_2O_3$ in binder) to specific gases, relative to $NO_2$, at the concentrations stated. Two sensors of each type were formed and tested.

TABLE 1

| GAS | ppm | 500 mg $Mn_2O_3$ | | 25 mg $Mn_2O_3$ | |
|---|---|---|---|---|---|
| | | Sensor 1 | Sensor 2 | Sensor 1 | Sensor 2 |
| SO2 | 5 | 1.53% | 0.81% | 0.86% | 0.79% |
| CO | 5 | 1.25% | 0.85% | 1.41% | 1.39% |
| H2 | 100 | 0.24% | 0.04% | 0.06% | 0.00% |
| CO2 | 50000 | 0.00% | 0.00% | 0.00% | 0.00% |
| NH3 | 20 | 0.42% | 0.18% | 0.09% | 0.06% |

Further experiments demonstrated that the quality of ozone filtering was unsatisfactory if the $Mn_2O_3$ powder was reduced to 5% or less by mass of the combined mixture of $Mn_2O_3$ and PTFE binder particles. Mixture of $Mn_2O_3$ powder with at least the same mass, and ideally more, of PTFE particles leads to the $Mn_2O_3$ coating the particles rather than forming solid masses.

For unmixed $Mn_2O_3$ powder (as specified in the Experimental Section above) we found that the ratio of the active surface area of filter material (by BET analysis) to the cross-sectional area of the filter (perpendicular to the gas path through the filter) was about 0.85 $m^2$ per $cm^2$. For $Mn_2O_3$ mixed with PTFE binder to 10% by mass of the combined mixture of $Mn_2O_3$ and binder, this ratio was 0.025 $m^2$ per $cm^2$ and for $Mn_2O_3$ mixed with PTFE binder to 8% by mass of the combined mixture it was 0.02 $m^2$ per $cm^2$.

Experiment 7

Figure 11:
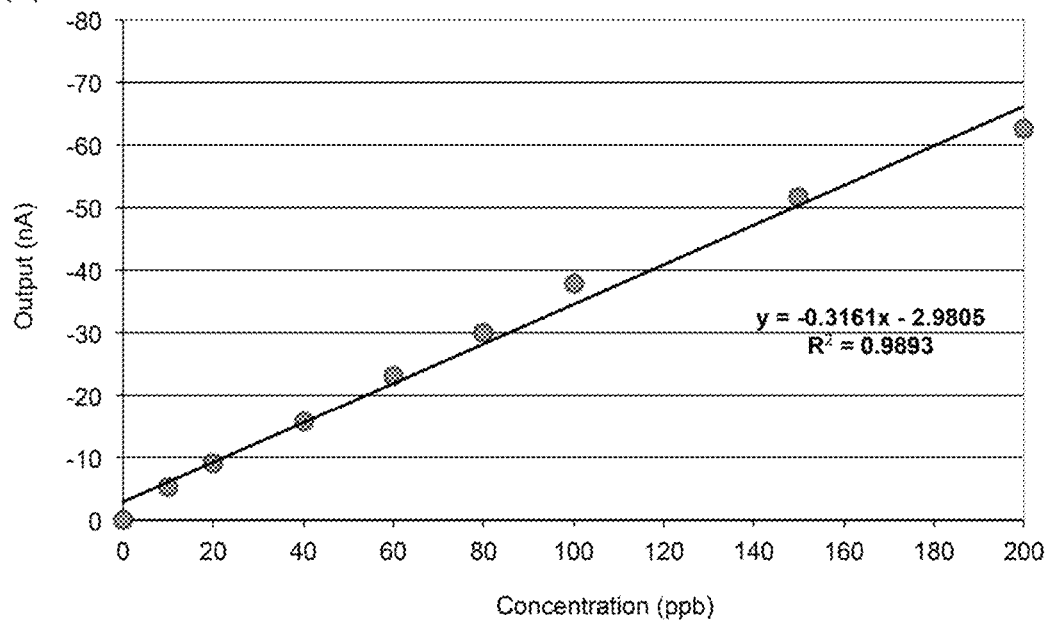
FIGS. 11A-11B shows the current response to a range of concentrations of $NO_2$ of sensors according to FIG. 2A (filtered) with filters comprising (A) 500 mg of powdered $Mn_2O_3$ and (B) 25 mg of powdered $Mn_2O_3$ mixed with 225 mg of PTFE particles having a size range of 710 µm to 1500 µm.
Figure 11:
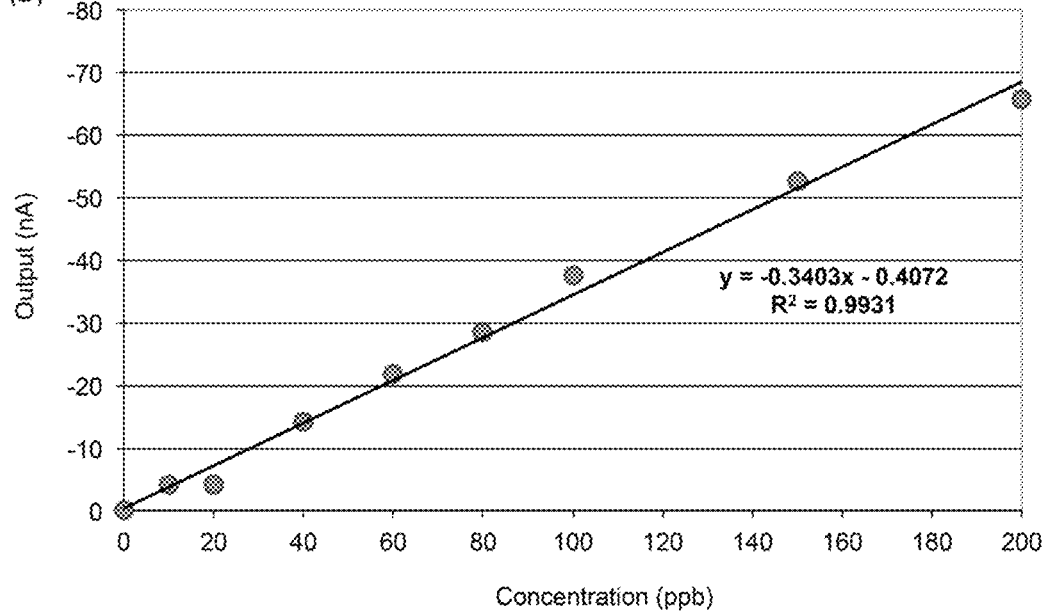

FIG. 11 shows the current response to a range of concentrations of $NO_2$ of sensors according to FIG. 2A (filtered) with filters comprising (A) 500 mg of powdered $Mn_2O_3$ and (B) 25 mg of powdered $Mn_2O_3$ mixed with 225 mg of PTFE particles having a size range of 710 µm to 1500 µm (i.e. 10% by weight of $Mn_2O_3$ in binder). The results show good sensitivity and linearity with $NO_2$ concentration with both the mixed with binder and unmixed filters.

Experiment 8

Figure 12:
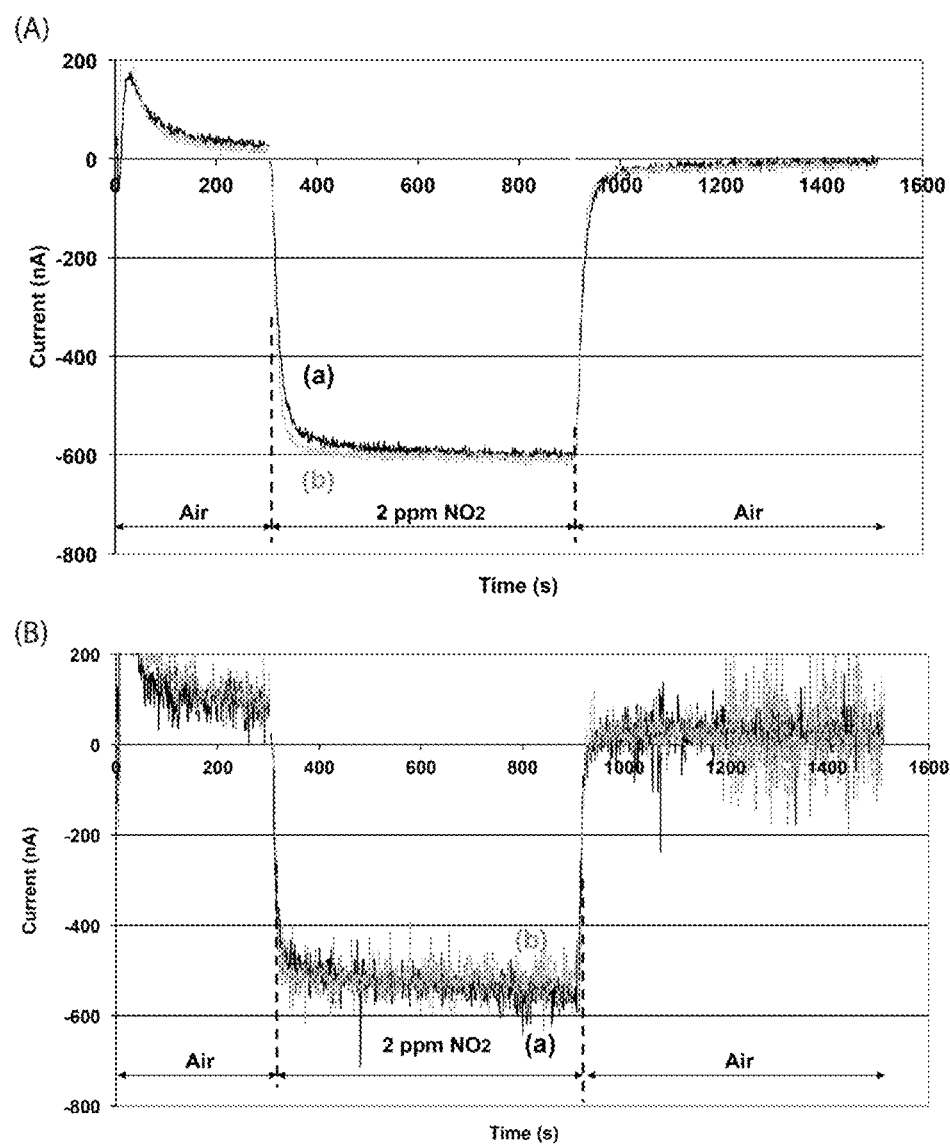
FIG. 12 shows the current response to 2 ppm $NO_2$ of sensors according to FIG. 2A (filtered) with filters comprising, in FIG. 12A, 500 mg of powdered $Mn_2O_3$ (a) 30 days after manufacture and (b) 173 days after manufacture and, in FIG. 12B, 25 mg of powdered $Mn_2O_3$ mixed with 225 mg of PTFE particles having a size range of 710 µm to 1500 µm (i.e. 10% by weight of in $Mn_2O_3$ in binder), (a) 19 days after manufacture and (b) 187 days after manufacture.

FIG. 12 shows the current response to 2 ppm $NO_2$ of sensors according to FIG. 2A (filtered) with filters comprising, in FIG. 12A, 500 mg of powdered $Mn_2O_3$ (a) 30 days after manufacture and (b) 173 days after manufacture and, in FIG. 12B, 25 mg of powdered $Mn_2O_3$ mixed with 225 mg of PTFE particles having a size range of 710 µm to 1500 µm (i.e. 10% by weight of $Mn_2O_3$ in binder), (a) 19 days after manufacture and (b) 187 days after manufacture.

The results demonstrate that sensors using $NO_2$ treated $Mn_2O_3$ powder, with or without dilution, shows a good and reproducible response to $NO_2$ 6 months after $NO_2$ treatment.

Experiment 9

Table 2 below shows the change with time (in days) of the cross sensitivity to 2 ppm NO (i.e. the ratio of the current response to 2 ppm NO to the current response to 2 ppm $NO_2$) of sensors according to FIG. 2A (filtered) with filters comprising 25 mg of powdered $MnO_2$ mixed with 225 mg of the PTFE particles having a size range of 710 µm to 1500 µm; 450 mg of powdered $MnO_2$ (not mixed with binder), 25 mg of powdered $Mn_2O_3$ mixed with 225 mg of PTFE particles having a size range of 710 µm to 1500 µm (i.e. 10% by weight of $Mn_2O_3$ in binder), and 500 mg of $Mn_2O_3$ (i.e. not mixed with binder) (a) 19 days after manufacture and (b) 187 days after manufacture.

TABLE 2

| Age (days) | ppm | 25 mg $MnO_2$ | 450 mg $MnO_2$ | 25 mg $Mn_2O_3$ | 500 mg $Mn_2O_3$ |
|---|---|---|---|---|---|
| 10 | 2 | 1.6 | 9.7 | 1.3 | 1.7 |
| 110 | 2 | 5.7 | 13.9 | 2.2 | 4.5 |
| 210 | 2 | 9.2 | 13.3 | 4.4 | 5.7 |

This shows that the cross-sensitivity to NO is lower when the ozone filter comprises powdered $Mn_2O_3$ than when the ozone filter comprises powdered $MnO_2$, and that the sensors in which $Mn_2O_3$ is mixed with PTFE give the best (lowest) cross-sensitivity to NO. Of particular benefit, the NO cross-sensitivity increases with time but this deterioration is reduced with powdered $Mn_2O_3$ in comparison to powdered $MnO_2$ and is minimised when powdered $Mn_2O_3$ is mixed with PTFE.

Experiment 10

Experiments were carried out to assess the temperature sensitivity of sensors according to FIG. 2B (unfiltered) (columns 2 and 3 below), and according to FIG. 2A (filtered) in which the ozone filter was 10% by weight of $Mn_2O_3$ powder in binder (after $NO_2$ treatment), 10% by weight of $Mn_2O_3$ powder in binder (without $NO_2$ treatment) and $NO_2$ treated $Mn_2O_3$ powder without binder (columns 4 through 6 below, respectively). The current response due to 2 ppm $NO_2$ at different temperatures, as a percentage of the current response due to 2 ppm $NO_2$ at 20° C. is shown in Table 3 below. The results show that, surprisingly, the ozone filter in which $Mn_2O_3$ powder was pretreated with $NO_2$ and mixed with PTFE has a much better current response at low temperatures than unmixed $Mn_2O_3$ powder and accordingly has a substantially better operating temperature range.

TABLE 3

| Temp. ° C. | No filter | No filter | 10 w/w % $Mn_2O_3$ $NO_2$ treated | 10 w/w % $Mn_2O_3$ not treated | 100 w/w % $Mn_2O_3$ $NO_2$ treated |
|---|---|---|---|---|---|
| −30 | 70 | 68 | 70 | 39 | −2 |
| −20 | 75 | 73 | 80 | 56 | 6 |
| −10 | 82 | 79 | 88 | 75 | 45 |
| 0 | 89 | 87 | 94 | 90 | 85 |
| 10 | 95 | 94 | 98 | 98 | 97 |
| 20 | 100 | 100 | 100 | 100 | 100 |
| 30 | 105 | 104 | 104 | 101 | 103 |
| 40 | 110 | 107 | 103 | 99 | 107 |
| 50 | 112 | 117 | 102 | 100 | 128 |

Experiment 11

In order to demonstrate that the ozone filter is useful with analytes other than $NO_2$, we modified a commercial electrochemical sensor for $SO_2$, having gold/ruthenium working and reference electrodes and a platinum black counter electrode (brand SO2-A4 available from Alphasense Limited, Great Notley, UK) by replacing an $H_2S$ filter with 25 mg of $Mn_2O_3$ powder mixed with 225 mg PTFE particles having a size range of 710 µm to 1500 µm, treated with $NO_2$ as above.

Figure 14:
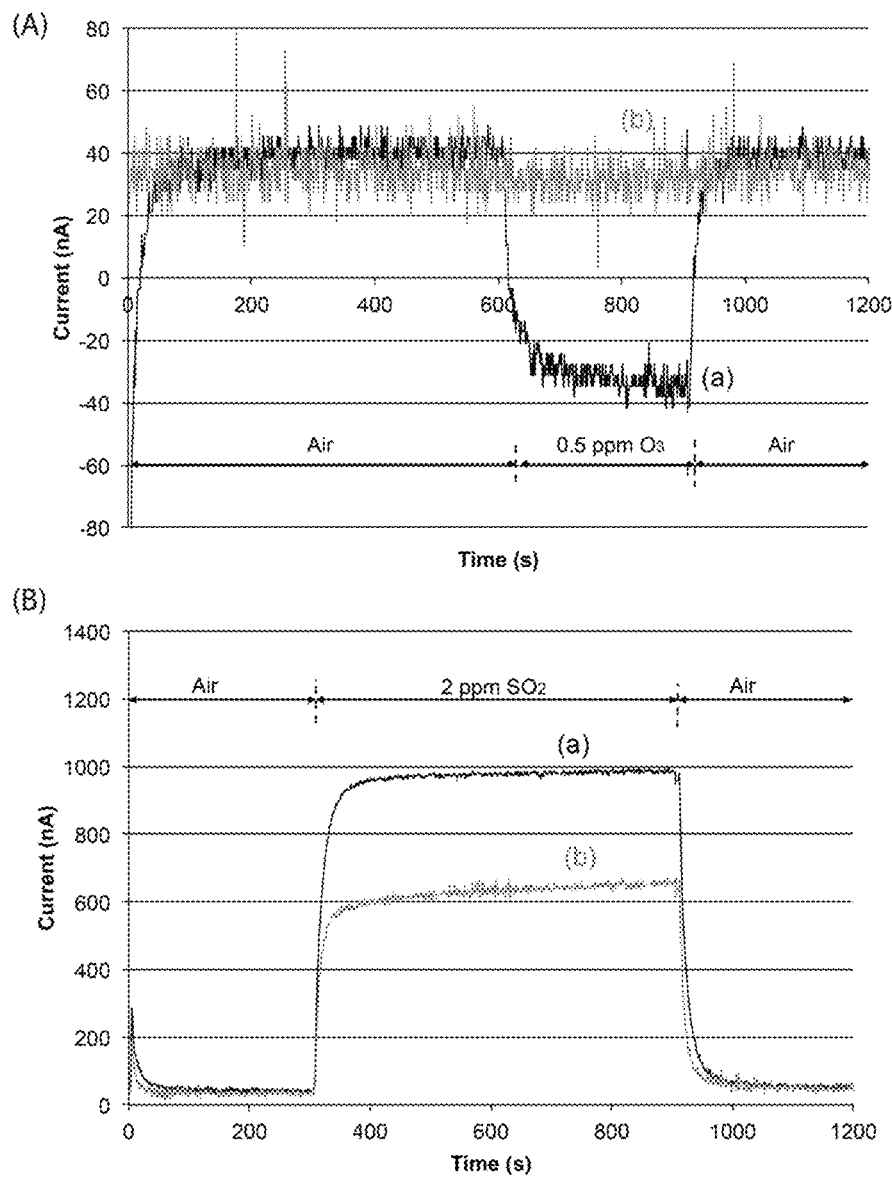
FIG. 14(A) shows the current response with time to air and then to 0.5 ppm $O_3$ of (a) an $SO_2$ sensor without an ozone filter, and (b) an $SO_2$ sensor with an ozone filter comprising 10% by weight of $Mn_2O_3$ powder in binder (after $NO_2$ treatment).
FIG. 14(B) shows the current response with time to air and then to 2 ppm $SO_2$ of (a) an SO2 sensor without an ozone filter, and (b) an SO2 sensor with an ozone filter comprising 10% by weight of Mn2O3 powder in binder (after NO2 treatment).

FIG. 14(A) shows the current response with time to air and then to 0.5 ppm $O_3$ of (a) an $SO_2$ sensor without an ozone filter, and (b) an $SO_2$ sensor with an ozone filter comprising 10% by weight of $Mn_2O_3$ powder in binder (after $NO_2$ treatment).

FIG. 14(B) shows the current response with time to air and then to 2 ppm $SO_2$ of (a) an $SO_2$ sensor without an ozone filter, and (b) an $SO_2$ sensor with an ozone filter comprising 10% by weight of $Mn_2O_3$ powder in binder (after $NO_2$ treatment).

The results demonstrate that the ozone filter can be used to remove ozone from a gas sample in an $SO_2$ sensor. Again, $O_3$ may be measured with a first sensor which has an electrode which is sensitive to $SO_2$ and $O_3$ and ozone filter according to the invention and a second sensor, also having an electrode which is sensitive to $SO_2$ and $O_3$, but no ozone filter, and comprising output signals.

Experiment 12

Figure 15:
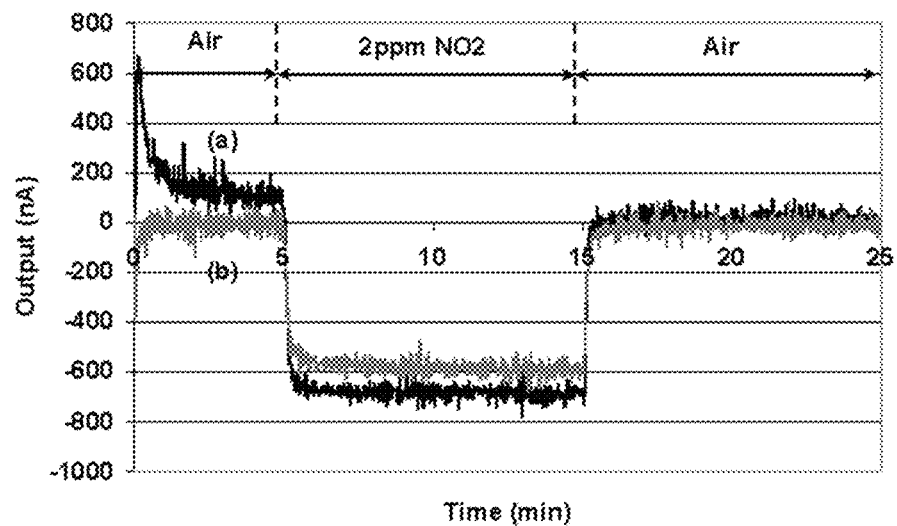
FIG. 15A shows the current response with to 2 ppm $NO_2$ and FIG. 15B shows the current response to 500 ppb $O_3$ of sensors (a) according to FIG. 2B (unfiltered) and (b) sensors according to FIG. 2A in which the filters were formed by 40 mg of powdered $Mn_2O_3$ mixed with 220 mg of 500 µm PTFE particles (i.e. 16% by weight of $Mn_2O_3$ in binder).
Figure 15:
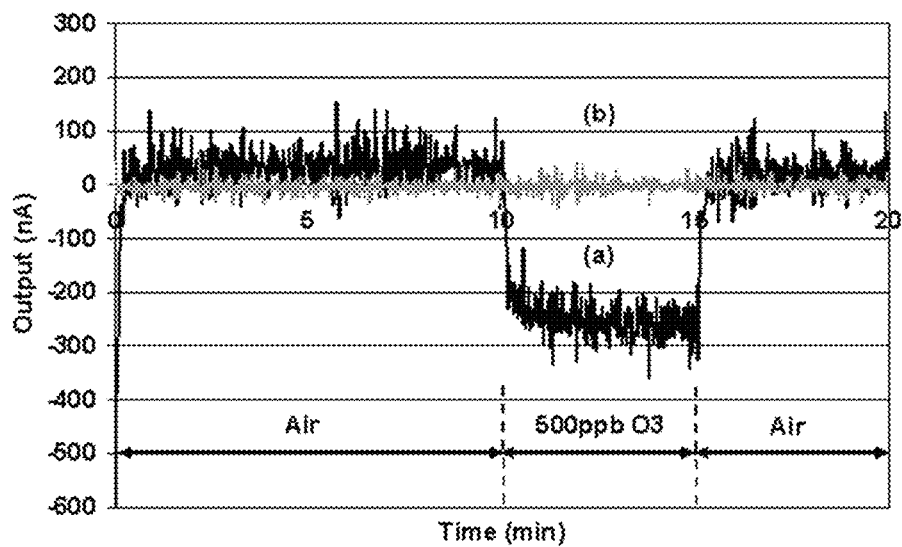

FIG. 15A shows the current response with to 2 ppm $NO_2$ and FIG. 15B shows the current response with time to 500 ppb $O_3$ of sensors (a) according to FIG. 2B (unfiltered) and (b) sensors according to FIG. 2A in which the filters were formed by 41.6 mg of powdered $Mn_2O_3$ mixed with 218.4 mg of 500 μm PTFE particles (i.e. 16% by weight of $Mn_2O_3$ in binder) and pretreated with $NO_2$ as described above.

No signal is observed in the presence of 500 ppb of $O_3$ (FIG. 15B, curve (b)) but a sensor which differs only by the omission of the filter gives a clearly defined current response (FIG. 15B, curve (a)). Thus we have found that a well-defined signal for $NO_2$ can be obtained with the sensors in which the filters were formed by 40 mg of powdered $Mn_2O_3$ mixed with 220 mg of 500 μm PTFE particles.

Experiment 13

Figure 2C:
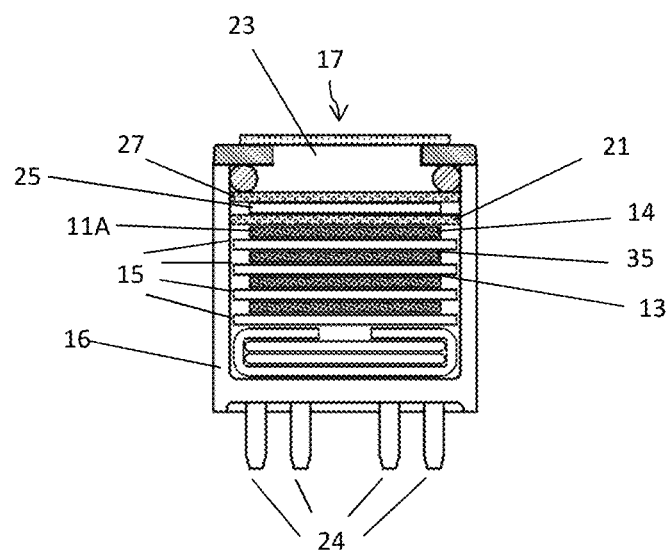
FIG. 2C is a replacement for the gas sensor of FIG. 2A employed (along with the sensor of FIG. 2B) in embodiments of the invention in which a solid $Mn_2O_3$ layer is used as filter.
Figure 16:
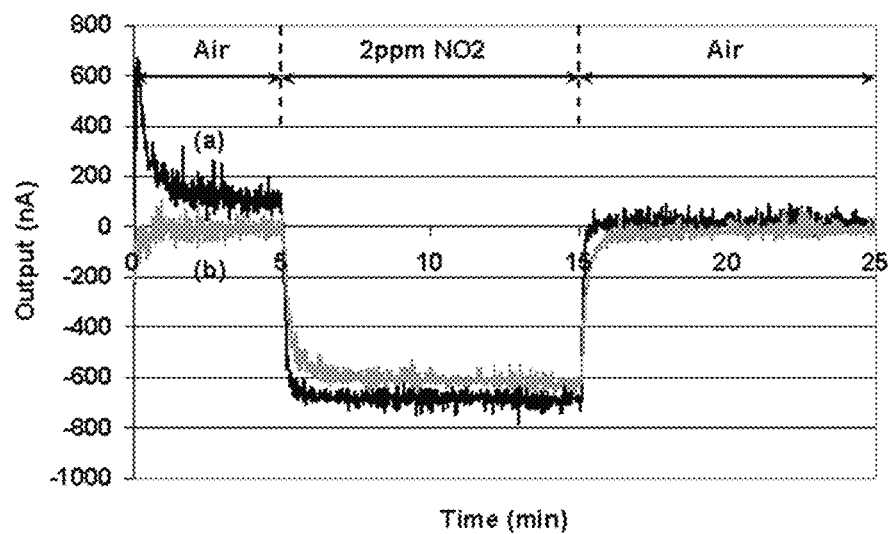
FIG. 16A shows the current response to 2 ppm $NO_2$ and FIG. 16B shows the current response to 500 ppb $O_3$ of sensors (a) according to FIG. 2B (unfiltered) and (b) sensors according to FIG. 2C in which the filters were formed by 25 mg of powdered $Mn_2O_3$ deposited onto a membrane (15 mg·cm$^{-2}$).
Figure 16:
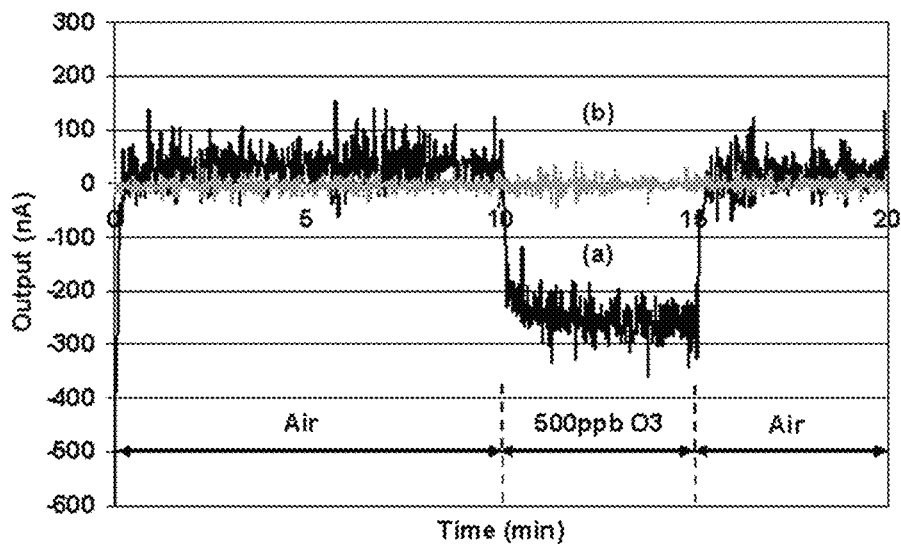

FIG. 16A shows the current response with time to 2 ppm $NO_2$ and FIG. 16B shows the current response with time to 500 ppb $O_3$ of sensors (a) according to FIG. 2B (unfiltered) and (b) sensors according to FIG. 2C in which the filters were formed by 25 mg of powdered $Mn_2O_3$ mixed with Fluon (Fluon is a trade mark) and deposited onto a membrane (15 mg·cm$^{-2}$).

Fluon comprises PTFE and a solvent and the resulting solid layer has about 26% PTFE by mass. Most of the $Mn_2O_3$ is therefore not associated with the PTFE particles and the purpose of the PTFE is to provide some porosity, as well as to make the material easier to handle in a manufacturing setting than unmixed $Mn_2O_3$.

No signal is observed in the presence of 500 ppb of $O_3$ (FIG. 16B, curve (b)) but a sensor which differs only by the omission of the filter gives a clearly defined current response (FIG. 16B, curve (a)). We have therefore found that a well-defined signal for $NO_2$ can be obtained with the sensors in which the filters were formed by a solid layer of 25 mg of powdered $Mn_2O_3$ deposited onto a membrane (15 mg·cm$^{-2}$).

Experiment 14

Figure 17:
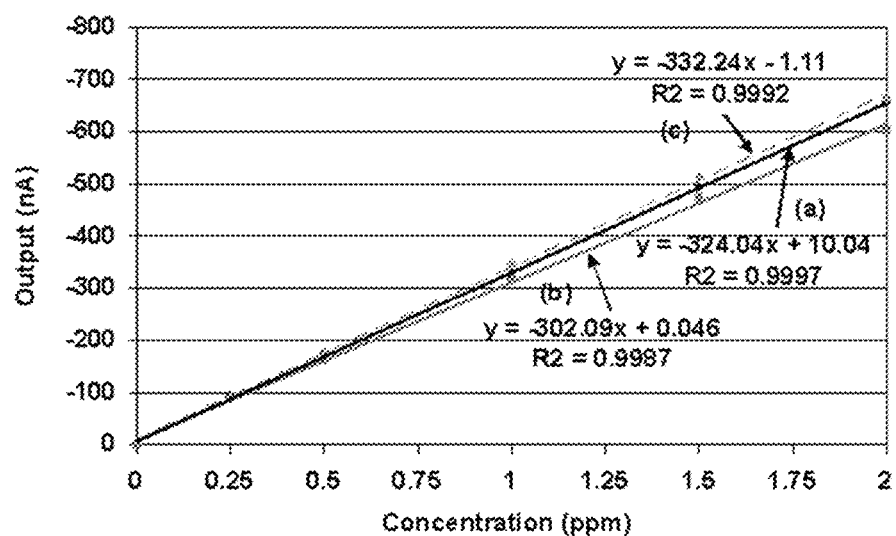
FIG. 17 shows the current response with time to a range of concentrations of $NO_2$ of sensors (a) according to FIG. 2B (unfiltered), (b) according to FIG. 2A with a filter comprising 40 mg of powdered $Mn_2O_3$ mixed with 220 mg of 500 µm PTFE particles and (c) according to FIG. 2C with 25 mg of powdered $Mn_2O_3$ deposited onto a membrane (15 mg·cm$^{-2}$).

FIG. 17 shows the current response to a range of concentrations of $NO_2$ of sensors (a) according to FIG. 2B (unfiltered), (b) according to FIG. 2A with a filter comprising 40 mg of powdered $Mn_2O_3$ mixed with 220 mg of 500 μm PTFE particles and (c) according to FIG. 2C with 25 mg of powdered $Mn_2O_3$ (again with about 26% PTFE by mass) and deposited onto a membrane (15 mg·cm$^{-2}$).

This demonstrates that powdered $Mn_2O_3$ pressed into a solid layer may form an effective ozone filter.

Experiment 15

Sensors according to FIG. 2A (filtered) were formed with filters comprising 500 mg of $Mn_2O_3$ (FIG. 18A) and (a) 40 mg of powdered $Mn_2O_3$ mixed with 220 mg of 500 μm PTFE particles, (b) 45 mg of powdered $Mn_2O_3$ mixed with 235 mg of 100 μm PTFE particles and (c) 100 mg of powdered $Mn_2O_3$, mixed with Fluon (Fluon is a trade mark), and deposited onto a membrane (30 mg·cm$^{-2}$) (FIG. 18B). In this case, the mass fraction of the deposited layer formed by PTFE is 15%. In contrast to Experiment 13, the $Mn_2O_3$ was pretreated with $NO_2$ by the process described above.

Figure 18:
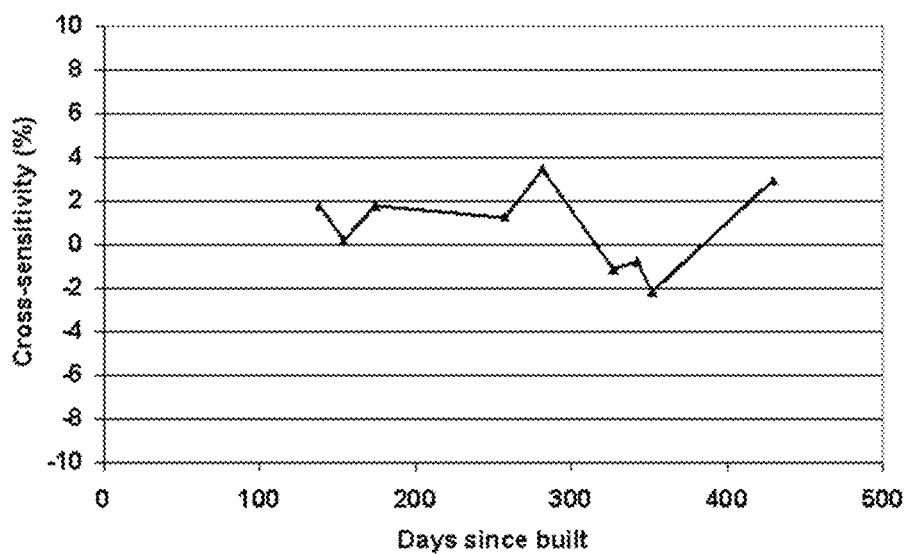
FIG. 18A is a plot of the variation with time in cross-sensitivity to $O_3$ (as a fraction of the sensitivity to $NO_2$) of a sensor according to FIG. 2A (filtered) containing 500 mg of powdered $Mn_2O_3$.
FIG. 18B is a similar plot to FIG. 18A of (a) a sensor according to FIG. 2A with a filter comprising 40 mg of powdered $Mn_2O_3$ mixed with 220 mg of 500 µm PTFE particles, (b) a sensor according to FIG. 2A with 45 mg of powdered $Mn_2O_3$ mixed with 235 mg of 100 µm PTFE particles and (c) a sensor according to FIG. 2C with 100 mg of powdered $Mn_2O_3$ deposited onto a membrane (30 mg·cm$^{-2}$).
Figure 18:
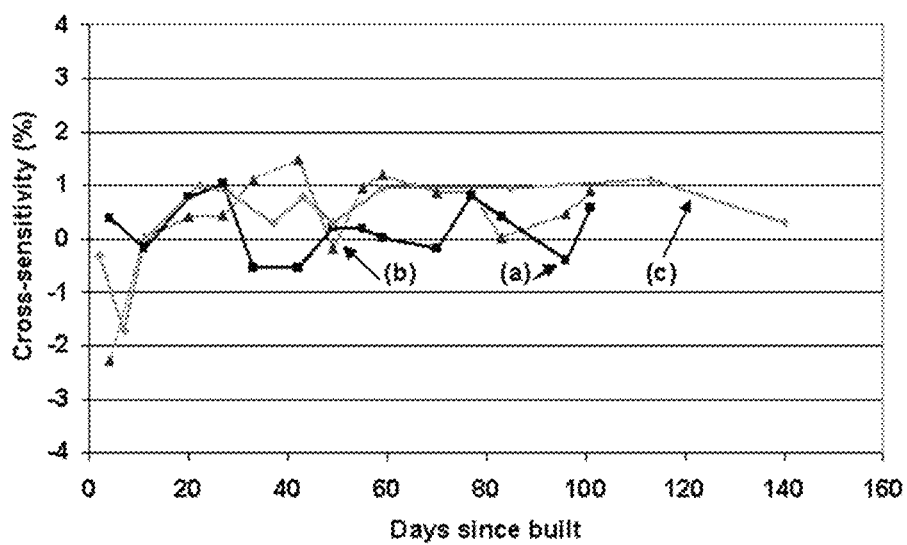

The sensors were exposed to 2 ppm $NO_2$ for 10 minutes and then to 500 ppb ozone $O_3$ for 5 minutes. FIG. 18 is a plot of the variation with time in cross-sensitivity of the sensors to $O_3$, i.e. the current response to $O_3$ as a fraction of the current response to a corresponding concentration (in this case 2 ppm) of $NO_2$.

These results demonstrate that $Mn_2O_3$ powder, whether unmixed, mixed with various PTFE particles sizes or as a solid layer deposited onto a membrane, forms an efficient ozone filter.

Although in the examples shown which use a solid layer, the layer comprises some PTFE in addition to $Mn_2O_3$, it is provided simply to ensure that the solid layer is microporous and can therefore be penetrated by analyte gas. Alternatively, $Mn_2O_3$ may be deposited by other means to give a microporous structure, for example by depositing $Mn_2O_3$. microparticles without binder, or screen printing optionally with glass or other particles. The PTFE is not required.

Furthermore, in further example embodiments, $Mn_2O_3$ powder, whether unmixed, or mixed with binder as described above, may be used in combination with a microporous solid $Mn_2O_3$ layer, to give a more robust sensor, for example for use in atmospheres with a particularly high concentration of $O_3$.

CONCLUSIONS

In the case of gas sensing apparatus for detecting $NO_2$ and/or $O_3$, the results demonstrate that $Mn_2O_3$ is useful as an ozone filter, whether as a powder or as a solid microporous layer. The cross sensitivity to NO can be reduced by mixing the $Mn_2O_3$ powder with binder, or by treating it with sufficient $NO_2$. Although these mixing or treatment steps could compromise ozone filtering, we have found that they have a greater effect in reducing cross sensitivity to NO and that it is therefore possible to obtain an efficient ozone filter with low cross sensitivity to NO.

What is claimed is:

1. An electrochemical gas sensing apparatus for sensing at least one gaseous analyte, the electrochemical gas sensing apparatus comprising a housing having an inlet, a sensing electrode configured to sense $NO_2$ and/or ozone and an ozone filter interposed between the sensing electrode and the inlet, wherein the ozone filter comprises $Mn_2O_3$ wherein the $Mn_2O_3$ is pre-treated by adsorbing to saturation at least $10^{12}$ molecules of $NO_2$ per cm$^2$ of surface of $Mn_2O_3$.

2. The electrochemical gas sensing apparatus according to claim 1, wherein the $Mn_2O_3$ is $Mn_2O_3$ powder.

3. The electrochemical gas sensing apparatus according to claim 2, wherein the ozone filter comprises the $Mn_2O_3$ powder mixed with binder particles.

4. The electrochemical gas sensing apparatus according to claim 3, wherein the ozone filter comprises the binder particles coated with the $Mn_2O_3$ powder.

5. The electrochemical gas sensing apparatus according to claim 1, wherein the ozone filter comprises a solid microporous layer which comprises the $Mn_2O_3$.

6. The electrochemical gas sensing apparatus according to claim 1, further comprising a second sensing electrode, wherein the second sensing electrode is in gaseous communication with a gas sample without an intervening ozone filter.

7. The electrochemical gas sensing apparatus according to claim 6, wherein the at least one gaseous analyte comprises ozone.

8. A method of sensing $NO_2$ and/or ozone comprising bringing the inlet of the electrochemical gas sensing apparatus according to claim 1 into gaseous communication with a gas sample.

9. A method of forming the electrochemical gas sensing apparatus of claim 1 for sensing the at least one gaseous analyte, the method comprising:
pre-treating the $Mn_2O_3$ with $NO_2$ by adsorbing to saturation the at least $10^{12}$ molecules of $NO_2$ per $cm^2$ of surface of $Mn_2O_3$;
providing the housing having the inlet and the sensing electrode configured to sense $NO_2$ and/or ozone; and
providing the ozone filter interposed between the sensing electrode and the inlet, wherein the ozone filter comprises the pre-treated $Mn_2O_3$.

10. The method of forming the electrochemical gas sensing apparatus according to claim 9, wherein the $Mn_2O_3$ is $Mn_2O_3$ powder mixed with binder particles.

11. The method of forming the electrochemical gas sensing apparatus according to claim 10 wherein the $Mn_2O_3$ powder coats the binder particles.

12. The method of forming the electrochemical gas sensing apparatus according to claim 9, wherein the filter comprises a solid microporous layer of $Mn_2O_3$.

13. The method of forming the electrochemical gas sensing apparatus according to claim 12, wherein the method comprises depositing a layer of $Mn_2O_3$ on a gas porous membrane.

14. The method of forming the electrochemical gas sensing apparatus according to claim 9, comprising providing a second sensing electrode in gaseous communication with a gas sample without an intervening ozone filter.

15. A method of sensing $NO_2$ and/or ozone comprising forming the electrochemical gas sensing apparatus by the method of claim 14, and exposing the gas sensing apparatus to a gas sample, wherein a difference in signals from the sensing electrode and the second sensing electrode is representative of ozone in the gas sample, and thereby determining from the signals from the sensing electrode and the second sensing electrode a concentration of $NO_2$ and/or ozone in the gas sample.

16. A method of sensing $NO_2$ and/or ozone comprising forming electrochemical gas sensing apparatus by the method of claim 9 and bringing the inlet into gaseous communication with a gas sample.

17. An electrochemical gas sensing apparatus for sensing at least one gaseous analyte, the electrochemical gas sensing apparatus comprising a housing having an inlet, a sensing electrode configured to sense $NO_2$ and/or ozone and an ozone filter interposed between the sensing electrode and the inlet, wherein the ozone filter comprises $Mn_2O_3$ wherein the $Mn_2O_3$ is pre-treated to saturation with at least $10^{12}$ molecules of $NO_2$ per $cm^2$ of surface of $Mn_2O_3$.

18. A method of forming the electrochemical gas sensing apparatus of claim 17 for sensing the at least one gaseous analyte, the method comprising:
pre-treating the $Mn_2O_3$ with $NO_2$ by saturating the at least $10^{12}$ molecules of $NO_2$ per $cm^2$ of surface of $Mn_2O_3$;
providing the housing having the inlet and the sensing electrode configured to sense $NO_2$ and/or ozone; and
providing the ozone filter interposed between the sensing electrode and the inlet, wherein the ozone filter comprises the pre-treated $Mn_2O_3$.

19. An electrochemical gas sensing apparatus for sensing at least one gaseous analyte, the electrochemical gas sensing apparatus comprising a housing having an inlet, a sensing electrode configured to sense $NO_2$ and/or ozone and an ozone filter interposed between the sensing electrode and the inlet, wherein the ozone filter comprises $Mn_2O_3$ which has in a pre-treatment been saturated with $NO_2$.

20. A method of forming the electrochemical gas sensing apparatus of claim 19 for sensing the at least one gaseous analyte, the method comprising:
pre-treating the $Mn_2O_3$ by saturating with $NO_2$;
providing the housing having the inlet and the sensing electrode configured to sense $NO_2$ and/or ozone; and
providing the ozone filter interposed between the sensing electrode and the inlet, wherein the ozone filter comprises the pre-treated $Mn_2O_3$.

* * * * *